(12) United States Patent
Mittmann

(10) Patent No.: US 12,383,353 B2
(45) Date of Patent: Aug. 12, 2025

(54) SYSTEM AND METHOD FOR EXCHANGING SURGICAL TOOLS IN AN IMPLANTABLE SURGICAL ROBOTIC SYSTEM

(71) Applicant: Vicarious Surgical Inc., Waltham, MA (US)

(72) Inventor: Elizabeth Mittmann, Cambridge, MA (US)

(73) Assignee: Vicarious Surgical Inc., Waltham, MA (US)

( * ) Notice: Subject to any disclaimer, the term of this patent is extended or adjusted under 35 U.S.C. 154(b) by 132 days.

(21) Appl. No.: 18/109,605

(22) Filed: Feb. 14, 2023

(65) Prior Publication Data

US 2023/0200920 A1    Jun. 29, 2023

Related U.S. Application Data

(63) Continuation of application No. PCT/US2021/058820, filed on Nov. 10, 2021.

(60) Provisional application No. 63/111,950, filed on Nov. 10, 2020.

(51) Int. Cl.
  *A61B 34/30* (2016.01)
  *A61B 34/00* (2016.01)

(52) U.S. Cl.
  CPC .............. *A61B 34/30* (2016.02); *A61B 34/71* (2016.02); *A61B 2034/305* (2016.02)

(58) Field of Classification Search
  CPC ... A61B 18/085; A61B 17/28; A61B 18/1442; A61B 34/30; A61B 34/71; A61B 17/29; A61B 2034/305; A61B 2017/00477; A61B 2017/2931; A61B 2017/00473
  See application file for complete search history.

(56) References Cited

U.S. PATENT DOCUMENTS

| | | | |
|---|---|---|---|
| 9,717,563 B2* | 8/2017 | Tognaccini | A61B 1/018 |
| 10,258,425 B2* | 4/2019 | Mustufa | A61B 34/37 |
| 10,285,765 B2 | 5/2019 | Sachs et al. | |
| 10,307,199 B2* | 6/2019 | Farritor | A61B 18/00 |
| 10,687,904 B2 | 6/2020 | Harris et al. | |
| 10,820,949 B2* | 11/2020 | Prisco | A61B 34/30 |
| 10,874,382 B2 | 12/2020 | Srivastava et al. | |
| 2002/0042620 A1 | 4/2002 | Julian et al. | |
| 2008/0249551 A1 | 10/2008 | Sunaoshi et al. | |

(Continued)

FOREIGN PATENT DOCUMENTS

| | | |
|---|---|---|
| EP | 3466347 A1 | 4/2019 |
| JP | 2008-253464 A | 10/2008 |
| WO | 2020/263870 A1 | 12/2020 |

OTHER PUBLICATIONS

Li et al., Development of a human-arm like laparoscopic instrument, 2016, IEEE, p. 68-70 (Year: 2016).*

(Continued)

*Primary Examiner* — McDieunel Marc
(74) *Attorney, Agent, or Firm* — McCarter & English, LLP

(57) ABSTRACT

An end effector region device of a robot arm that forms part of a surgical robotic system that includes a tool base portion that is coupled to an end portion of the robot arm by a connector and first and second pulley elements that are rotatably coupled to the tool base portion. The device further includes first and second tool elements that are coupled together and can be removably and replaceably mounted to the pulley elements.

42 Claims, 22 Drawing Sheets

(56) References Cited

U.S. PATENT DOCUMENTS

| | | | |
|---|---|---|---|
| 2018/0049824 A1 | 2/2018 | Harris et al. | |
| 2018/0049828 A1* | 2/2018 | Robinson | A61B 34/76 |
| 2018/0221102 A1 | 8/2018 | Wang et al. | |
| 2018/0272543 A1 | 9/2018 | Kayama et al. | |
| 2019/0076199 A1 | 3/2019 | Kline et al. | |
| 2019/0142531 A1 | 5/2019 | Wentworth et al. | |
| 2019/0336199 A1 | 11/2019 | Worrell et al. | |
| 2020/0246092 A1* | 8/2020 | Robinson | A61B 34/30 |
| 2020/0405423 A1 | 12/2020 | Schuh | |
| 2021/0282874 A1* | 9/2021 | Hussain | A61B 90/39 |

OTHER PUBLICATIONS

Anderson et al., Comparing a Mechanical Analogue With the Da Vinci User Interface: Suturing at Challenging Angles, 3016, IEEE, p. 1060-1065 (Year: 2016).*

Shang et al., A Single-Port Robotic System for Transanal Microsurgery—Design and Validation, 2017, IEEE, p. 1510-1517 (Year: 2017).*

Bajaj et al., State of the Art in Artificial Wrists: A Review of Prosthetic and Robotic Wrist Design, 2019, IEEE, p. 261-277 (Year: 2019).*

International Search Report and Written Opinion for Application No. PCT/US2021/058820, dated Feb. 1, 2022, 7 pages.

European Office Action for Application No. 21892748.1, dated May 2, 2024, 9 pages.

Japanese Office Action for Application No. 2023-510431, dated May 13, 2025, 6 pages.

\* cited by examiner

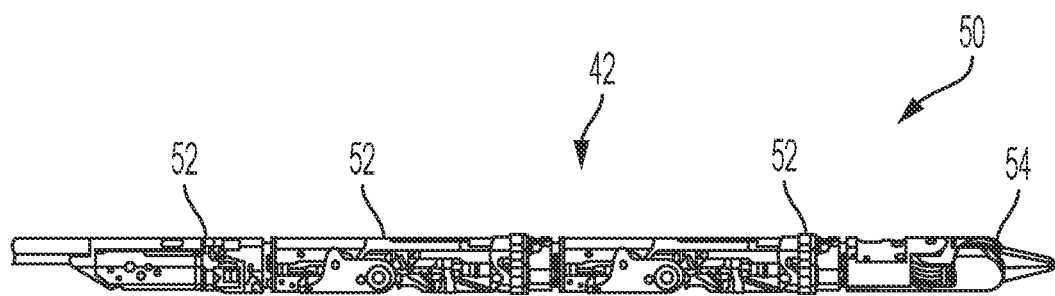
FIG. 2A
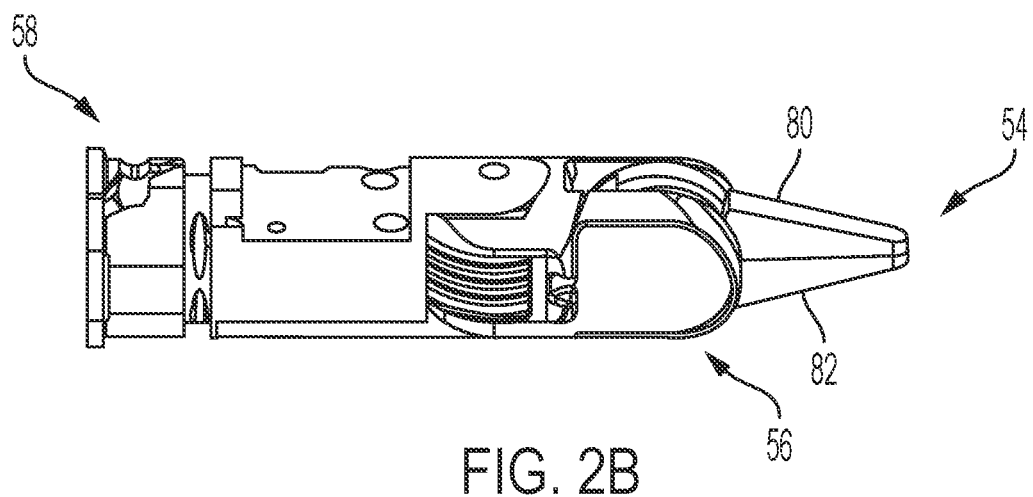
FIG. 2B
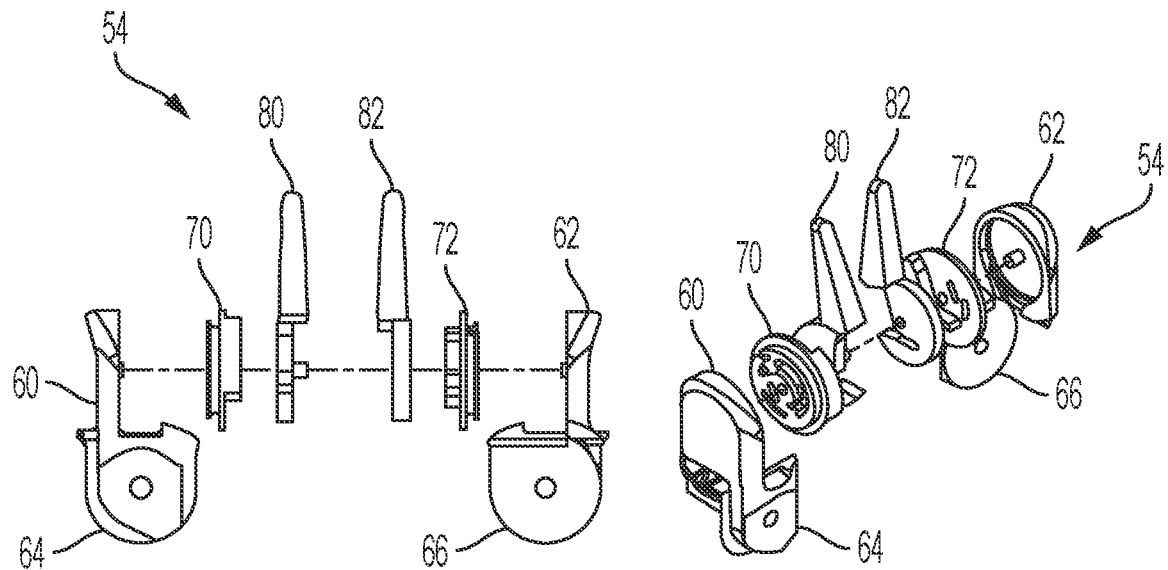
FIG. 3
FIG. 4

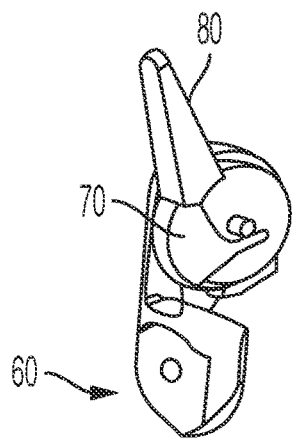
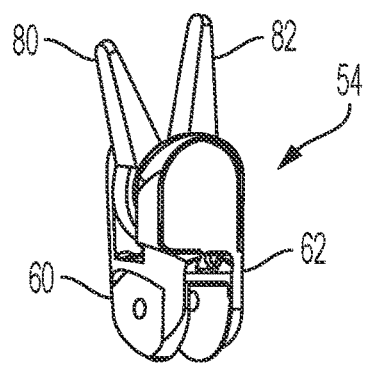
FIG. 5  FIG. 6
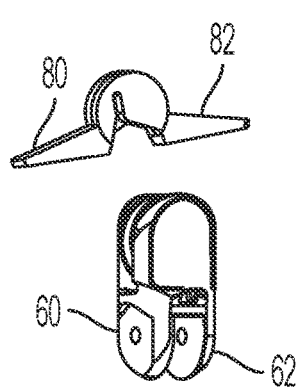
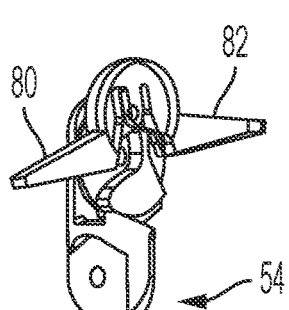
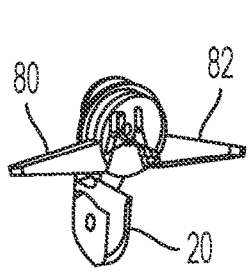
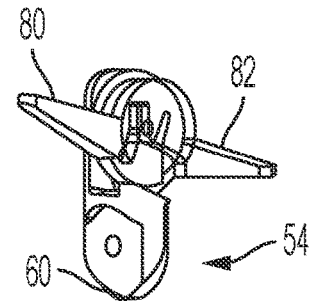
FIG. 7A    FIG. 7B    FIG. 7C    FIG. 7D

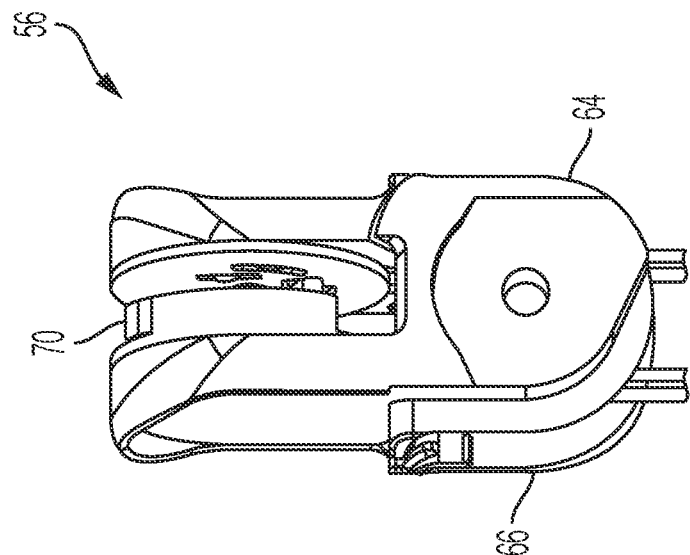
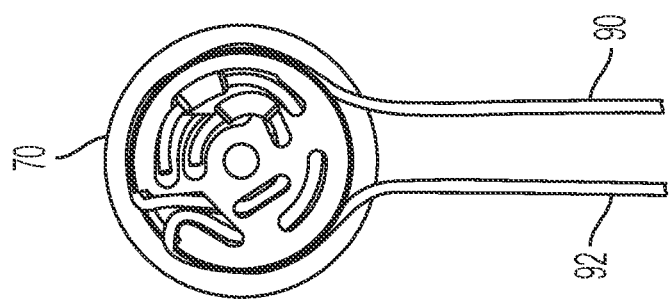
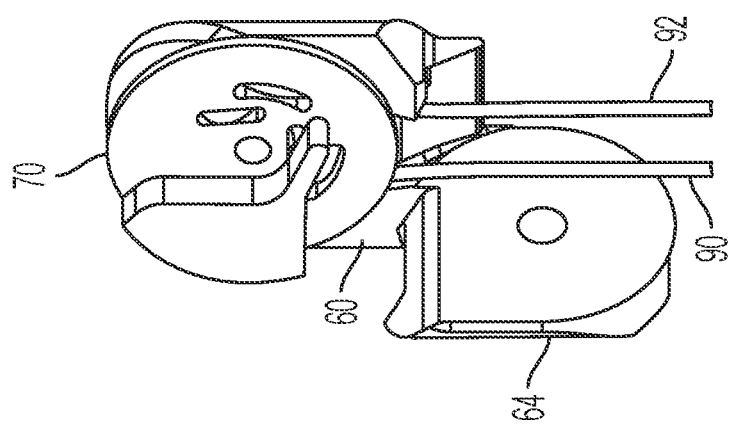

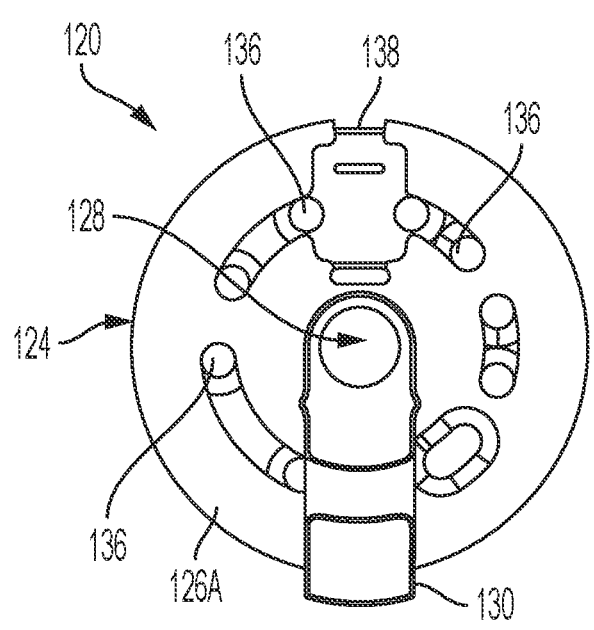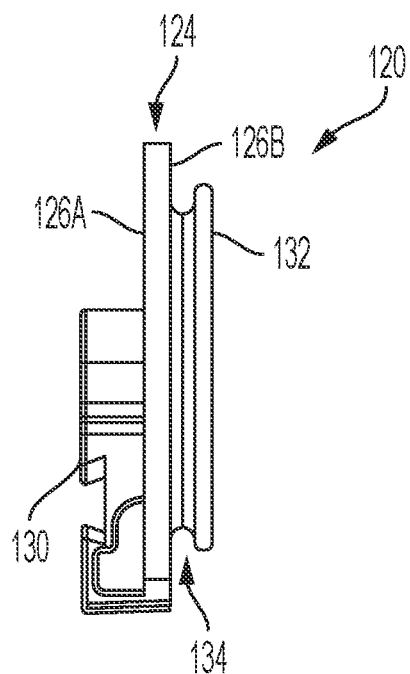
FIG. 16A  FIG. 16B
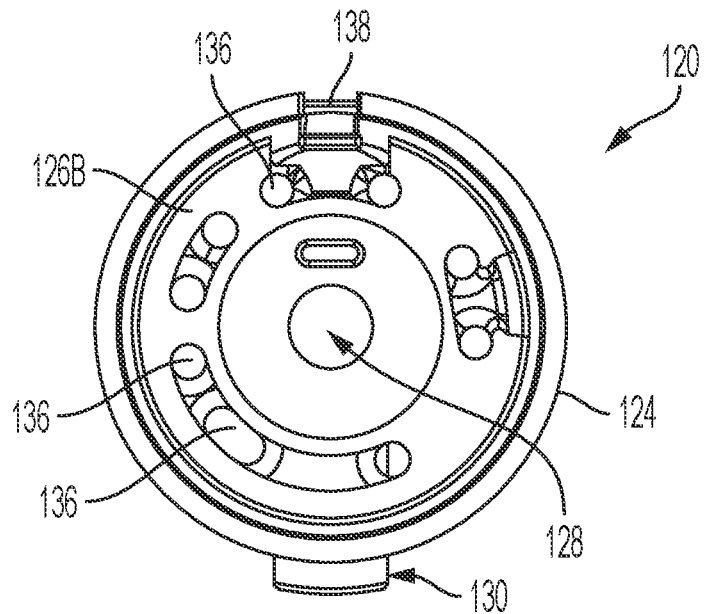
FIG. 16C

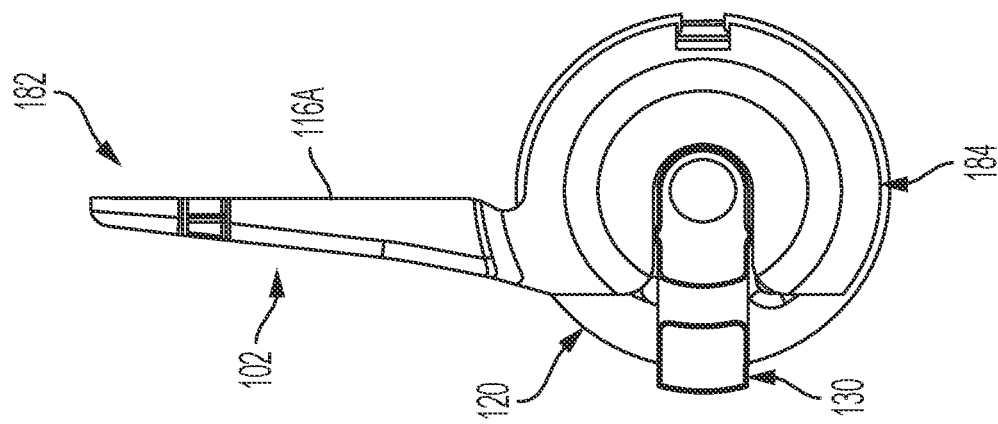
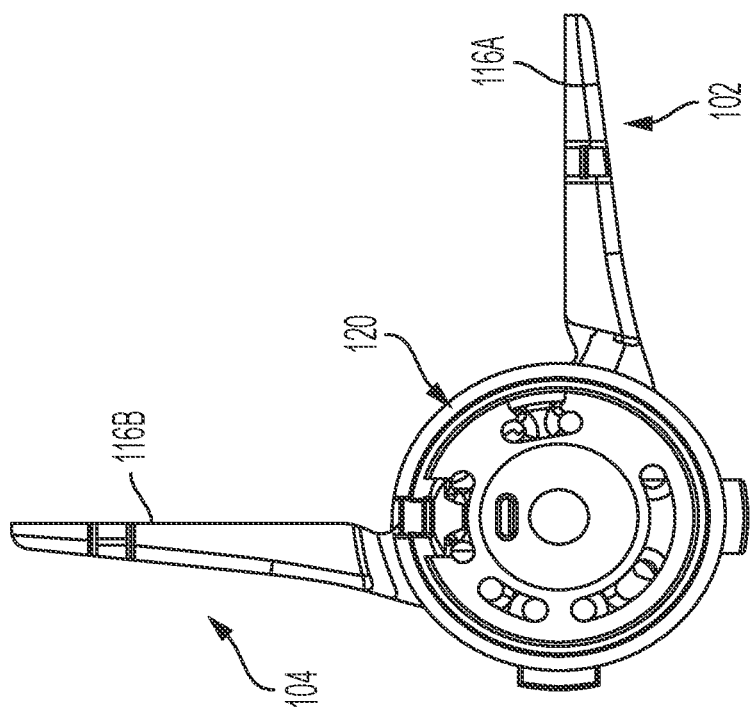

SYSTEM AND METHOD FOR EXCHANGING SURGICAL TOOLS IN AN IMPLANTABLE SURGICAL ROBOTIC SYSTEM

RELATED APPLICATION

The present application is a continuation of PCT/US2021/058820, filed Nov. 10, 2021, which claims priority to U.S. provisional patent application Ser. No. 63/111,950, filed on Nov. 10, 2020, and entitled System And Method For Exchanging Surgical Tools In An Implantable Surgical Robotic System, the contents of each of which are herein incorporated by reference.

BACKGROUND OF THE INVENTION

Since its inception in the early 1990s, the field of minimally invasive surgery has rapidly grown. While minimally invasive surgery vastly improves patient outcome, this improvement comes at a cost to the surgeon's ability to operate with precision and ease. During conventional laparoscopic procedures, the surgeon typically inserts a laparoscopic instrument through multiple small incisions in the patient's abdominal wall. The nature of tool insertion through the abdominal wall constrains the motion of the laparoscopic instruments as the instruments are unable to move side-to-side without injury to the abdominal wall. Standard laparoscopic instruments are also limited in motion, and are typically limited to four axes of motion. These four axes of motion are movement of the instrument in and out of the trocar (axis 1), rotation of the instrument within the trocar (axis 2), and angular movement of the trocar in two planes while maintaining the pivot point of the trocar's entry into the abdominal cavity (axes 3 and 4). For over two decades, the majority of minimally invasive surgery has been performed with only these four degrees of motion. Moreover, prior systems require multiple incisions if the surgery requires addressing multiple different locations within the abdominal cavity.

Existing robotic surgical devices attempted to solve many of these problems. Some existing robotic surgical devices replicate non-robotic laparoscopic surgery with additional degrees of freedom at the end of the instrument. However, even with many costly changes to the surgical procedure, existing robotic surgical devices have failed to provide improved patient outcome in the majority of procedures for which they are used. Additionally, existing robotic devices create increased separation between the surgeon and surgical end-effectors. This increased separation causes injuries resulting from the surgeon's misunderstanding of the motion and the force applied by the robotic device. Because the degrees of freedom of many existing robotic devices are unfamiliar to a human operator, surgeons need extensive training on robotic simulators before operating on a patient in order to minimize the likelihood of causing inadvertent injury.

To control existing robotic devices, a surgeon typically sits at a console and controls manipulators with his or her hands and/or feet. Additionally, robot cameras remain in a semi-fixed location, and are moved by a combined foot and hand motion from the surgeon. These semi-fixed cameras offer limited fields of view and often result in difficulty visualizing the operating field.

Other robotic devices have two robotic manipulators inserted through a single incision. These devices reduce the number of incisions required to a single incision, often in the umbilicus. However, existing single-incision robotic devices have significant shortcomings stemming from their actuator design. Existing single-incision robotic devices include servomotors, encoders, gearboxes, and all other actuation devices within the in vivo robot, which results in relatively large robotic units that are inserted within the patient. This size severely constrains the robotic unit in terms of movement and ability to perform various procedures. Further, such a large robot typically needs to be inserted through a large incision site, oftentimes near the size of open surgery, thus increasing risk of infection, pain, and general morbidity.

Further, in laparoscopic and robotic surgeries, a variety of tools and graspers are needed to complete a surgical procedure. Initially inserting all of the necessary tools to be employed by the surgical robotic system at once within the patient can result in an increased risk to the patient due to the possible use of excess incision sites and the inherent increased complexity of safely storing and manipulating the tools during the surgical procedure. Thus, the current surgical procedures typically rely on removing and replacing tools throughout the surgery. This removal and replacement process serves to lengthen the time of the surgery, increasing the possibility of complications as tools are fully removed and new tools are inserted within the patient, and increasing the amount of material needed for and hence the potential cost of the surgery.

SUMMARY OF THE INVENTION

The present invention is directed to the ability to swap out tools that form the end effectors of the robot arms of the present invention in an easy and efficient manner. The ability to easily swap out tools allows the user, such as the surgeon, to only remove and replace the end effector portion of the robot arm rather than replace the entire robot arm, which typically has a dedicated tool attached thereto. The tool element removal and replacement can be done within or external to the patient. Since the entire robot arm does not need to be replaced, the robot arm of the present invention reduces costs and waste since the user does not need to employ an entire suite of robot arms.

The invention includes an end effector portion that includes a pair of opposed tool exchange base segments, pulley elements, electrical contact elements, and tool elements, shown as a pair of grasper elements. The tool base is assembled by mounting the pulley elements to their respective tool base segments by inserting a portion of the pulley elements into a recess formed in the tool base segments. The end effector portion can then be coupled to the robot arm assembly by a pair of connecting flanges and coupling pin, each of which has an opening formed therein. The opening can be coupled to a suitable connector formed at an end portion of the robot arm assembly. The pulley elements can employ surface features, such as bosses, that are complementary in shape to surface features formed in or on the main body of the tool elements. When the bosses of the pulley elements and the openings formed in the tool elements are oriented in a selected position (e.g., open tool exchange position), then the tool elements can be easily mounted thereon or removed from the tool base portion. The tool elements can be disposed in the open tool exchange position where the grasper portions (e.g., working surfaces) are separated from each other by a predetermined set angle, such as for example about 180 degrees. This allows the tool elements to easily slide on the surface features of the pulley elements. Once mounted, the pulley elements can be actuated by suitable cables so as to move the tool elements into one or more use positions where the working surfaces are separated from each other by less than 180 degrees. The use positions secure the tool elements together while concomitantly securing the tool elements to the tool base portion. To remove the tool elements from the tool base, the tool elements can once again be disposed in the open tool exchange position.

The present invention is directed to a method for removing from and inserting on a wrist portion of a robot arm in a surgical robotic system one or more tool elements that form a tool instrument. The method includes providing a tool base portion that is coupled to an end portion of the robot arm, rotatably coupling first and second pulley elements to the tool base portion, securing the first and second pulley elements to the tool base portion with an axle element, providing first and second tool elements that are coupled together, and configuring the first and second tool elements to be positioned into an open tool exchange position so as to be able to be mounted on or removed from the tool base portion. The tool base portion can be configured to include a first tool base segment and a second tool base segment, and the first pulley element is rotatably coupled to the first tool base segment and the second pulley element is rotatably coupled to the second tool base segment. As such, the first and second tool elements are removably and replaceably coupled to the tool base portion when disposed in the open tool exchange position.

The method of the present invention further includes configuring the first pulley element to have a first pulley surface feature formed thereon and configuring the second pulley element to have a second pulley surface feature formed thereon, and configuring the first tool element to have a first surface feature formed thereon that is complementary in shape to the first pulley surface feature of the first pulley element and configuring the second tool element to have a second surface feature formed thereon that is complementary in shape to the second pulley surface feature of the second pulley element. When the first and second pulley surface features of the first and second pulley elements are aligned and when the first and second surface features of the first and second tool elements are aligned when disposed in the open tool exchange position, the first and second tool elements can be removably and replaceably mounted on the first and second pulley surface features of the first and second pulley elements, respectively.

The method also includes, according to one embodiment, providing a first tool element that can be coupled together with a second tool element, configuring the first tool element to have a first connection surface feature formed thereon, and configuring the second tool element to have a second connection surface feature formed thereon that is complementary in shape to the first connection surface feature, such that the first and second connection surface features, when aligned, enable the first and second tool elements to be coupled together. The first connection surface feature can include a groove and the second connection surface feature can include a protruding rail-like element. The first and second connection surface features, in combination, form a dove-tail joint connection. Further, when the first tool element and the second tool element are assembled, the method includes locking the first and second tool elements together by selectively rotating one or more of the first and second tool elements out of the open tool exchange position and into one or more use positions by rotational movement of one or more of the first and second pulley elements. This enables the device of the present invention to easily remove and replace different types of tool elements from the tool base portion when disposed in a selected position, such as for example the open tool exchange position, while locking the tool elements together and to the tool base portion by moving the tool elements out of the open tool exchange position into one or more different use positions. The use positions correspond to the positions that the tool elements would be placed in during the performance of a surgical procedure. According to one practice, the tool elements would not need to be separated by an angular distance approaching or exceeding 180 degrees during use.

The method of the present invention also includes providing a first conductive spring element that is coupled to the first pulley element and a second conductive spring element that is coupled to the second pulley element, and providing a first conductive contact element that is coupled to the first tool element and a second conductive contact element that is coupled to the second tool element. The method further includes maintaining direct contact between a portion of the conductive spring element and a portion of the conductive contact element, during use, and which is independent of a rotational position of the first and second pulley elements.

The present invention is also directed to an end effector region device of a robot arm in a surgical robotic system that includes a tool base portion that is coupled to an end portion of the robot arm by a connector, a first pulley element that is rotatably coupled to the tool base portion, a second pulley element that is rotatably coupled to the tool base portion, wherein the first and second pulley elements are secured to the tool base portion with an axle element, and a first tool element that is coupled together with a second tool element. The first and second tool elements are configured to be positioned into an open tool exchange position so as to be able to be mounted on or removed from the tool base portion. The tool base portion can include according to one embodiment a first tool base segment and a second tool base segment, and the first pulley element is rotatably coupled to the first tool base segment and the second pulley element is rotatably coupled to the second tool base segment. The first and second tool elements are removably and replaceably coupled to the tool base portion when disposed in the open tool exchange position.

The first pulley element has a first pulley surface feature formed thereon and the second pulley element has a second pulley surface feature formed thereon, and the first tool element has a first surface feature formed thereon that is complementary in shape to the first pulley surface feature of the first pulley element and the second tool element has a second surface feature formed thereon that is complementary in shape to the second pulley surface feature of the second pulley element. The first and second pulley surface features of the first and second pulley elements are aligned and the first and second surface features of the first and second tool elements are aligned when they are disposed in the open tool exchange position. In this position, the first and second tool elements can be removably and replaceably mounted on the first and second pulley surface features of the first and second pulley elements, respectively.

Still further, the first tool element has a first connection surface feature formed thereon and the second tool element has a second connection surface feature formed thereon that is complementary in shape to the first connection surface feature, such that the first and second connection surface features, when aligned, enable the first and second tool elements to be coupled together. The first connection surface feature includes a groove and the second connection surface feature includes a protruding rail-like element. The first and second connection surface features can be configured to form a dove-tail joint connection.

Still further, when the first tool element and the second tool element are assembled, the first and second tool elements are locked together by selective rotation of one or more the first and second tool elements out of the open tool exchange position and into one or more use positions by rotational movement of one or more of the first and second pulley elements.

The device of the present invention can also include a first conductive spring element that is coupled to the first pulley element and a second conductive spring element that is coupled to the second pulley element, and a first conductive contact element that is coupled to the first tool element and a second conductive contact element that is coupled to the second tool element. When assembled together, a portion of the conductive spring element continually and directly contacts a portion of the conductive contact element, during use, and independent of a rotational position of the first and second pulley elements.

The present invention is also directed to a wrist portion of a robot arm forming part of a robotic unit of a surgical robotic system, comprising a tool base portion that is coupled to an end portion of the robot arm by a connector, a first pulley element rotatably coupled to the tool base portion, wherein the first pulley element has a main body having a first pulley surface feature formed thereon, a second pulley element rotatably coupled to the tool base portion, wherein the second pulley element has a main body having a second pulley surface feature formed thereon, a first tool element having a main body having a first surface feature formed thereon that is complementary in shape to the first pulley surface feature of the first pulley element, and a second tool element having a main body having a second surface feature formed thereon that is complementary in shape to the second pulley surface feature of the second pulley element. The first pulley surface feature of the first pulley element and the second pulley surface feature of the second pulley element are aligned with each other when disposed in a first open tool exchange position. In this position, the first and second tool elements can be removably and replaceably mounted on the first and second pulley surface features of the first and second pulley elements, respectively. According to one embodiment, the tool base portion comprises a first tool base segment and a second tool base segment, and the first pulley element is rotatably coupled to the first tool base segment and the second pulley element is rotatably coupled to the second tool base segment. Further, when the first and second tool elements are removably mounted on the first and second pulley elements, the first surface feature of the first tool element mates with and seats on the first pulley surface feature of the first pulley element and the second surface feature of the second tool element mates with and seats on the second pulley surface feature of the second pulley element. According to one embodiment, each of the first and second pulley surface features is shaped and configured as a boss element and each of the first and second surface features includes a slot.

The tool base segments of the present invention also have a main body having an extension portion at one end and a flange portion at an opposed end. The extension portion has an inner surface and an opposed outer surface and has an aperture formed therein. The inner surface of the extension portion has a recess formed therein. The flange portion of each of the first and second tool base segments has an opening formed therein for seating the connector. Further, each of the first and second pulley elements has a main body having an inner surface and an opposed outer surface having a connection element formed thereon and protruding outwardly therefrom. The pulley surface features are formed on the inner surface of the main body. The main body of each of the first and second pulley elements has a plurality of holes formed therein, and at least a portion of the plurality of holes are sized and configured for seating a portion of a control cable. Still further, the connection element of the first pulley element seats and is retained within the recess formed in the inner surface of the first tool base segment, and the connection element of the second pulley element seats and is retained within the recess formed in the inner surface of the second tool base segment.

The wrist portion also includes a first electrically conductive spring element coupled to the first pulley element and a second electrically conductive spring element coupled to the second pulley element. Each of the first and second electrically conductive spring elements comprises a main body having a central coil element, a top tab portion coupled to one end of the coil element, and a bottom tab portion coupled to another end of the coil element. The bottom tab portion is coupled to an electrical lead wire housed within the tool base portion, and the coil element is coupled to the outer surface of the pulley element and at least a portion of the top tab portion is coupled to the inner surface of the pulley element. During use, the central coil element is configured to expand and contract based on movement of the top tab portion.

According to the present invention, the wrist portion can include a first conductive contact element coupled to a working surface of the first tool element, and a second conductive contact element coupled to a working surface of the second tool element. Further, at least a portion of the first and second conductive contact elements are configured for contacting at least a portion of the top tab portion of the first and second conductive spring elements, respectively, when mounted to the first and second tool elements, respectively. Still further, the contact portion of each of the first and second conductive contact elements remains in continual electrical contact with the respective portion of the first and second conductive spring elements, during use.

BRIEF DESCRIPTION OF THE DRAWINGS

These and other features and advantages of the present invention will be more fully understood by reference to the following detailed description in conjunction with the attached drawings in which like reference numerals refer to like elements throughout the different views. The drawings illustrate principals of the invention and, although not to scale, show relative dimensions.

FIGS. 2A and 2B are perspective views of a robot arm of a robotic unit according to the teachings of the present invention.

FIGS. 3 and 4 are exploded perspective views of the end effector portion of the robot arm according to a first embodiment of the present invention.

FIG. 5 is a partial assembled view of a portion of the end effector portion of the robot arm according to the teachings of the present invention.

FIG. 6 is a perspective view of a fully assembled end effector portion of the robot arm according to the teachings of the present invention.

FIGS. 7A-7D are perspective views of the tool base portion of the end effector portion and a selected end effector tool according to the teachings of the present invention.

FIGS. 12A-12C are partial perspective views of selected components of the tool base portion showing the cables for driving the pulley elements of the present invention.

FIGS. 16A-16C are front, side, and rear views, respectively, of the pulley element of the end effector portion of the robot arm according to the teachings of the present invention.

FIG. 26A is a rear perspective view of the tool elements when mounted to the pulley element according to the teachings of the present invention.

FIG. 26B is a front perspective view of a tool element when mounted to a corresponding pulley element according to the teachings of the present invention.

DETAILED DESCRIPTION

Figure 1:
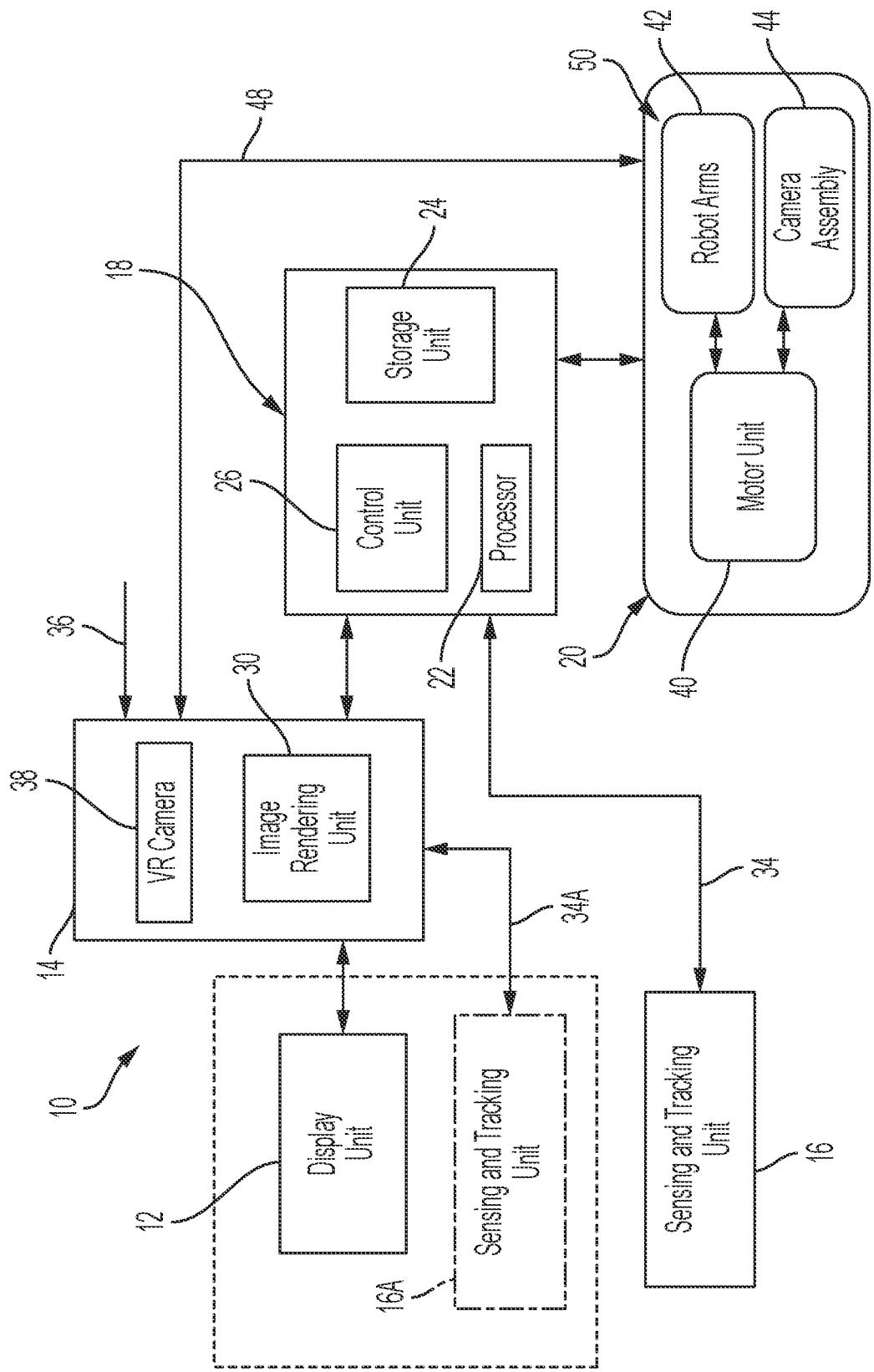
FIG. 1 is a schematic illustration of an exemplary surgical robotic system that implements the robot end effectors of the present invention.

In the following description, numerous specific details are set forth regarding the system and method of the present invention and the environment in which the system and method may operate, in order to provide a thorough understanding of the disclosed subject matter. It will be apparent to one skilled in the art, however, that the disclosed subject matter may be practiced without such specific details, and that certain features, which are well known in the art, are not described in detail in order to avoid complication and enhance clarity of the disclosed subject matter. In addition, it will be understood that any examples provided below are merely illustrative and are not to be construed in a limiting manner, and that it is contemplated by the present inventors that other systems, apparatuses, and/or methods can be employed to implement or complement the teachings of the present invention and are deemed to be within the scope of the present invention.

While the system and method of the present invention can be designed for use with one or more surgical robotic systems employed as part of a virtual reality surgical system, the robotic system of the present invention may be employed in connection with any type of surgical system, including for example robotic surgical systems, straight-stick type surgical systems, and laparoscopic systems. Additionally, the system of the present invention may be used in other non-surgical systems, where a user requires access to a myriad of information, while controlling a device or apparatus.

The present invention employs a robotic subsystem that includes a surgical robotic unit that can be inserted into a patient via a trocar through a single incision point or site. The robotic unit is small enough to be deployed in vivo at the surgical site and is sufficiently maneuverable when inserted to be able to move within the body so as to perform various surgical procedures at multiple different points or sites. The surgical robotic unit includes multiple separate robotic arms that are deployable within the patient along different or separate axes. Further, a surgical camera assembly can also be deployed along a separate axis. Thus, the surgical robotic unit employs multiple different components, such as a pair of robotic arms and a surgical or robotic camera assembly, each of which are deployable along different axes and are separately manipulatable, maneuverable, and movable. The robotic arms and the camera assembly that are disposable along separate and manipulatable axes is referred to herein as the Split Arm (SA) architecture. The SA architecture is designed to simplify and increase efficiency of the insertion of robotic surgical instruments through a single trocar at a single insertion site, while concomitantly assisting with deployment of the surgical instruments into a surgical ready state as well as the subsequent removal of the surgical instruments through the trocar. By way of example, a surgical instrument can be inserted through the trocar to access and perform an operation in vivo in the abdominal cavity of a patient. In some embodiments, various surgical instruments may be utilized, including but not limited to robotic surgical instruments, as well as other surgical instruments known in the art.

The system and method disclosed herein can be incorporated and utilized with the robotic surgical device and associated system disclosed for example in U.S. Pat. No. 10,285,765 and in PCT patent application Serial No. PCT/US20/39203, and/or with the camera assembly and system disclosed in United States Publication No. 2019/0076199, where the content and teachings of all of the foregoing patents, patent applications and publications are incorporated herein by reference. The surgical robotic unit that forms part of the present invention can form part of a surgical robotic system that includes a surgeon workstation that includes appropriate sensors and displays, a user workstation, and a robot support system (RSS) for interacting with and supporting the robotic subsystem of the present invention. The robotic subsystem includes a motor unit and an surgical robotic unit that includes one or more robot arms and one or more camera assemblies. The robot arms and camera assembly can form part of a single support axis robotic system or can form part of the split arm (SA) architecture robotic system. The robot support system can provide multiple degrees of freedom such that the robotic unit can be maneuvered within the patient into a single position or multiple different positions. In one embodiment, the robot support system can be directly mounted to a surgical table or to the floor or ceiling within an operating room. In another embodiment, the mounting is achieved by various fastening means, including but not limited to, clamps, screws, or a combination thereof. In other embodiments, the structure may be free standing. The robot support system can mount a motor assembly that is coupled to the surgical robotic unit, which includes the robot arms and the camera assembly. The motor assembly can include gears, motors, drivetrains, electronics, and the like, for powering the components of the surgical robotic unit.

The robot arms and the camera assembly are capable of multiple degrees of freedom of movement. According to one practice, when the robot arms and the camera assembly are inserted into a patient through the trocar, they are capable of movement in at least the axial, yaw, pitch, and roll directions. The robot arm assemblies are designed to incorporate and utilize a multi-degree of freedom of movement robotic arm with an end effector mounted at a distal end thereof that corresponds to a wrist area or joint of the user. In other embodiments, the working end (e.g., the end effector end) of the robot arm is designed to incorporate and utilize other robotic surgical instruments, such as for example the surgical instruments set forth in U.S. Publ. No. 2018/0221102, the contents of which are herein incorporated by reference.

FIG. 1 is a schematic block diagram description of a surgical robotic system 10 according to the teachings of the present invention. The system 10 includes a display device or unit 12, a virtual reality (VR) computing unit 14, a sensing and tracking unit 16, a computing unit 18, and a robotic subsystem 20. The display unit 12 can be any selected type of display for displaying information, images or video generated by the VR computing unit 14, the computing unit 18, and/or the robotic subsystem 20. The display unit 12 can include or form part of for example a head-mounted display (HMD), a screen or display, a three-dimensional (3D) screen, and the like. The display unit can also include an optional sensor and tracking unit 16A, such as can be found in commercially available head mounted displays. The sensing and tracking units 16 and 16A can include one or more sensors or detectors that are coupled to a user of the system, such as for example a nurse or a surgeon. The sensors can be coupled to the arms of the user and if a head-mounted display is not used, then additional sensors can also be coupled to a head and/or neck region of the user. The sensors in this arrangement are represented by the sensor and tracking unit 16. If the user employs a head-mounted display, then the eyes, head and/or neck sensors and associated tracking technology can be built-in or employed within that device, and hence form part of the optional sensor and tracking unit 16A. The sensors of the sensor and tracking unit 16 that are coupled to the arms of the surgeon can be preferably coupled to selected regions of the arm, such as for example the shoulder region, the elbow region, the wrist or hand region, and if desired the fingers. According to one practice, the sensors are coupled to a pair of hand controllers that are manipulated by the surgeon. The sensors generate position data indicative of the position of the selected portion of the user. The sensing and tracking units 16 and/or 16A can be utilized to control movement of the camera assembly 44 and the robotic arms 42 of the robotic subsystem 20. The position data 34 generated by the sensors of the sensor and tracking unit 16 can be conveyed to the computing unit 18 for processing by a processor 22. The computing unit 20 can determine or calculate from the position data 34 the position and/or orientation of each portion of the surgeon's arm and convey this data to the robotic subsystem 20. According to an alternate embodiment, the sensing and tracking unit 16 can employ sensors coupled to the torso of the surgeon or any other body part. Further, the sensing and tracking unit 16 can employ in addition to the sensors an Inertial Momentum Unit (IMU) having for example an accelerometer, gyroscope, magnetometer, and a motion processor. The addition of a magnetometer is standard practice in the field as magnetic heading allows for reduction in sensor drift about the vertical axis. Alternate embodiments also include sensors placed in surgical material such as gloves, surgical scrubs, or a surgical gown. The sensors may be reusable or disposable. Further, sensors can be disposed external of the user, such as at fixed locations in a room, such as an operating room. The external sensors can generate external data 36 that can be processed by the computing unit and hence employed by the system 10. In other embodiments, there are sensors located on a mechanical linkage that the user manipulates. The sensors generate signals that serve as inputs to be processed by the computing unit. According to another embodiment, when the display unit 12 is a head mounted device that employs an associated sensor and tracking unit 16A, the device generates tracking and position data 34A that is received and processed by the VR computing unit 14. Further, the sensor and tracking unit 16 can include if desired a hand controller. The displays, sensing and tracking units, VR computing unit and the like can form part of a surgeon or remote work station.

In the embodiment where the display is a HMD, the display unit 12 can be a virtual reality head-mounted display, such as for example the Oculus Rift, the Varjo VR-1 or the HTC Vive Pro Eye. The HMD can provide the user with a display that is coupled or mounted to the head of the user, lenses to allow a focused view of the display, and a sensor and/or tracking system 16A to provide position and orientation tracking of the display. The position and orientation sensor system can include for example accelerometers, gyroscopes, magnetometers, motion processors, infrared tracking, eye tracking, computer vision, emission and sensing of alternating magnetic fields, and any other method of tracking at least one of position and orientation, or any combination thereof. As is known, the HMD can provide image data from the camera assembly 44 to the right and left eyes of the surgeon. In order to maintain a virtual reality experience for the surgeon, the sensor system can track the position and orientation of the surgeon's head, and then relay the data to the VR computing unit 14, and if desired to the computing unit 18. The computing unit 18 can further adjust the pan and tilt of the camera assembly 44 of the robot so as to follow the movement of the user's head.

The sensor or position data 34A generated by the sensors if associated with the HMD, such as for example associated with the display unit 12 and/or tracking unit 16A, can be conveyed to the computing unit 18 either directly or via the VR computing unit 14. Likewise, the tracking and position data 34 generated by the other sensors in the system, such as from the sensing and tracking unit 16 that can be associated with the user's arms and hands, can be conveyed to the computing unit 18. The tracking and position data 34, 34A can be processed by the processor 22 and can be stored for example in the storage unit 24. The tracking and position data 34, 34A can also be used by the control unit 26, which in response can generate control signals for controlling movement of one or more portions of the robotic subsystem 20. The robotic subsystem 20 can include a user workstation, the robot support system (RSS), a motor unit 40, and an implantable surgical robotic unit 50 that includes one or more robot arms 42 and one or more camera assemblies 44. According to one embodiment, the motor unit 40 can form part of the robot support system. The implantable robot arms 42 and camera assembly 44 can form part of a single support axis robotic unit, such as that disclosed and described in U.S. Pat. No. 10,285,765, or can form part of a split arm (SA) architecture robot system, such as that disclosed and described in PCT patent application no. PCT/US20/39203.

The control signals generated by the control unit 26 can be received by the motor unit 40 of the robotic subsystem 20. The motor unit 40 can include a series of servomotors and gears that are configured for driving separately the robot arms 42 and the cameras assembly 44 of the robotic unit 50. The robot arms 42 can be controlled to follow the scaled-down movement or motion of the surgeon's arms as sensed by the associated sensors. The robot arms 42 can have portions or regions that can be associated with movements associated with the shoulder, elbow, and wrist joints as well as the fingers of the user. For example, the robotic elbow joint can follow the position and orientation of the human elbow, and the robotic wrist joint can follow the position and orientation of the human wrist. The robot arms 42 can also have associated therewith end regions that can terminate in end-effectors or graspers that follow the movement of one or more fingers of the user, such as for example the index finger as the user pinches together the index finger and thumb. While the arms of the robot follow movement of the arms of the user, the robot shoulders are fixed in position. In one embodiment, the position and orientation of the torso of the user is subtracted from the position and orientation of the users arms. This subtraction allows the user to move his or her torso without the robot arms moving.

The robot camera assembly 44 is configured to provide the surgeon with image data 48, such as for example a live video feed of an operation or surgical site, as well as enable a surgeon to actuate and control the cameras forming part of the camera assembly 44. The camera assembly 44 preferably includes a pair of cameras, the optical axes of which are axially spaced apart by a selected distance, known as the inter-camera distance, so as to provide a stereoscopic view or image of the surgical site. The surgeon can control the movement of the cameras either through movement of a head-mounted display or via sensors coupled to the head of the surgeon, or by using a hand controller or sensors tracking the user's head or arm motions, thus enabling the surgeon to obtain a desired view of an operation site in an intuitive and natural manner. The cameras are movable in multiple directions, including for example in the yaw, pitch and roll directions, as is known. The components of the stereoscopic cameras can be configured to provide a user experience that feels natural and comfortable. In some embodiments, the interaxial distance between the cameras can be modified to adjust the depth of the operation site perceived by the user.

According to one embodiment, the camera assembly 44 can be actuated by movement of the surgeon's head. For example, during an operation, if the surgeon wishes to view an object located above the current field of view (FOV), the surgeon looks in the upward direction, which results in the stereoscopic cameras being rotated upward about a pitch axis from the user's perspective. The image or video data 48 generated by the camera assembly 44 can be displayed on the display unit 12. If the display unit 12 is a head-mounted display, the display can include the built-in tracking and sensor system 16A that obtains raw orientation data for the yaw, pitch and roll directions of the HMD as well as positional data in Cartesian space (x, y, z) of the HMD. However, alternative tracking systems may be used to provide supplementary position and orientation tracking data of the display in lieu of or in addition to the built-in tracking system of the HMD.

The image data 48 generated by the camera assembly 44 can be conveyed to the virtual reality (VR) computing unit 14 and can be processed by the VR or image rendering unit 30. The image data 48 can include still photographs or image data as well as video data. The VR rendering unit 30 can include suitable hardware and software for processing the image data and then rendering the image data for display by the display unit 12, as is known in the art. Further, the VR rendering unit 30 can combine the image data received from the camera assembly 44 with information associated with the position and orientation of the cameras in the camera assembly, as well as information associated with the position and orientation of the head of the surgeon. With this information, the VR rendering unit 30 can generate an output video or image rendering signal and transmit this signal to the display unit 12. That is, the VR rendering unit 30 renders the position and orientation readings of the hand controllers and the head position of the surgeon for display in the display unit, such as for example in a HMD worn by the surgeon.

The VR computing unit 14 can also include a virtual reality (VR) camera unit 38 for generating one or more virtual reality (VR) cameras for use or emplacement in the VR world that is displayed in the display unit 12. The VR camera unit 38 can generate one or more virtual cameras in a virtual world, and which can be employed by the system 10 to render the images for the head-mounted display. This ensures that the VR camera always renders the same views that the user wearing the head-mounted display sees to a cube map. In one embodiment, a single VR camera can be used and in another embodiment separate left and right eye VR cameras can be employed to render onto separate left and right eye cube maps in the display to provide a stereo view. The FOV setting of the VR camera can self-configure itself to the FOV published by the camera assembly 44. In addition to providing a contextual background for the live camera views or image data, the cube map can be used to generate dynamic reflections on virtual objects. This effect allows reflective surfaces on virtual objects to pick up reflections from the cube map, making these objects appear to the user as if they're actually reflecting the real world environment.

The robotic subsystem 20 can employ multiple different robotic arms 42 that are deployable along different or separate axes. Further, the camera assembly 44, which can employ multiple different camera elements, can also be deployed along a common separate axis. Thus, the surgical robotic unit employs multiple different components, such as a pair of separate robotic arms and a camera assembly 44, which are deployable along different axes. Further, the robot arms 42 and the camera assembly 44 are separately manipulatable, maneuverable, and movable. The robotic subsystem 20, which includes the robot arms and the camera assembly, is disposable along separate manipulatable axes to form the SA architecture. The SA architecture is designed to simplify and increase efficiency of the insertion of robotic surgical instruments through a single trocar at a single insertion point or site, while concomitantly assisting with deployment of the surgical instruments into a surgical ready state, as well as the subsequent removal of the surgical instruments through the trocar. By way of example, a surgical instrument can be inserted through the trocar to access and perform an operation in vivo in a body cavity of a patient. In some embodiments, various surgical instruments may be utilized, including but not limited to robotic surgical instruments, as well as other surgical instruments known in the art.

In some embodiments, the robotic subsystem 20 of the present invention is supported by a structure with multiple degrees of freedom such that the robotic arms 42 and camera assembly 44 (e.g., robotic unit 50) can be maneuvered within the patient into a single position or multiple different positions. In some embodiments, the robotic subsystem 20 can be directly mounted to a surgical table or to the floor or ceiling within an operating room, or to any other types of support structure. In other embodiments, the mounting is achieved by various fastening means, including but not limited to clamps, screws, or a combination thereof. In still further embodiments, the support structure may be free standing. The support structure is referred to herein as the robot support system (RSS). The RSS can form part of an overall surgical robotic system 10 that can include a virtual station that allows a surgeon to perform virtual surgery within the patient.

In some embodiments, the RSS of the surgical robotic system 10 can optionally include the motor unit 40 that is coupled to the robotic unit 50 at one end and to an adjustable support member or element at an opposed end. Alternatively, as shown herein, the motor unit 40 can form part of the robotic subsystem 20. The motor unit 40 can include gears, one or more motors, drivetrains, electronics, and the like, for powering and driving one or more components of the robot arms and the camera assembly (e.g., robotic unit 50). The robotic unit 50 can be selectively coupled to the motor unit 40. According to one embodiment, the RSS can include a support member that has the motor unit 40 coupled to a distal end thereof. The motor unit 40 in turn can be coupled to the camera assembly 44 and to each of the robot arms 42. The support member can be configured and controlled to move linearly, or in any other selected direction or orientation, one or more components of the robotic unit 50.

The motor unit 40 can also provide mechanical power, electrical power, mechanical communication, and electrical communication to the robotic unit 50, and can further include an optional controller for processing input data from one or more of the system components (e.g., the display 12, the sensing and tracking unit 16, the robot arms 42, the camera assembly 44, and the like), and for generating control signals in response thereto. The motor unit 40 can also include a storage element for storing data. Alternatively, the motor unit 40 can be controlled by the computing unit 18. The motor unit 40 can thus generate signals for controlling one or more motors that in turn can control and drive the robot arms 42, including for example the position and orientation of each articulating joint of each arm, as well as the camera assembly 44. The motor unit 40 can further provide for a translational or linear degree of freedom that is first utilized to insert and remove each component of the robotic unit 50 through a suitable medical device, such as a trocar 108. The motor unit 40 can also be employed to adjust the inserted depth of each robot arm 42 when inserted into the patient 100 through the trocar 108.

The present invention is directed to the ability to swap out tools that form the end effectors of the robot arms of the present invention in an easy and efficient manner. The ability to easily swap out tools allows the user, such as the surgeon, to only remove and replace the end effector portion of the robot arm rather than replace the entire robot arm, which typically has a dedicated tool attached thereto. The tool element removal and replacement can be done within or external to the patient. Since the entire robot arm does not need to be replaced, the robot arm of the present invention reduces costs and waste since the user does not need to employ an entire suite of robot arms and associated tools.

FIGS. 2A and 2B illustrate the general design of selected components of a robot arm 42 of the surgical robotic unit 50 according to a first embodiment of the present invention that allows the user to replace the end effectors of the robot arm without requiring the replacement of the entire robot arm. As such, the end effector region of the robot arms of the present invention provides for a highly functional, easy to use, mechanical connection that allows for the easy removal and replacement of tools. For the sake of simplicity, only a single robot arm is shown, although a second robot arm or subsequent robot arms can be similar or identical in form and function. The illustrated robot arm 42 can include a series of articulation segments 52 that form joint sections that correspond to the joints of a human arm. As such, the articulation segments 52 can be constructed and combined to provide for rotational and/or hinged movement so as to emulate different portions of the human arm, such as for example the shoulder joint or region, elbow joint or region, and the wrist joint or region 58. The articulation segments 52 of the robot arm 42 are constructed to provide cable-driven, rotational movement, for example, but within the confines of reasonable rotational limits. The articulation segments 52 are configured to provide maximum torque and speed with minimum size. The articulation segments 52 are mechanically coupled together and end in an end effector portion or segment 54. The end effector portion 54 includes a tool base portion 56 that can incorporate therein any selected surgical tool to be employed so as to perform a desired or selected surgery. For example, the tool base portion 56 mounts a pair of tool elements 80, 82. In the current example, the tool elements are grippers, although those of ordinary skill in the art will readily recognize that any selected type of surgical tool can be employed. As shown in FIG. 2B, the end effector portion 54 and the adjacent arm segment 52 form a wrist portion or joint 58 of the robot arm. The end effector portion 54 is shown in detail for example in FIGS. 3-12C.

As shown in FIGS. 2A-6, the end effector portion 54 includes opposed tool base segments 60 and 62, pulley elements 70 and 72, and tool elements 80 and 82, shown as a pair of gripper or grasper elements. The tool base portion 56 is assembled by mounting the pulley element 70 to the tool base segment 60 via a protrusion, such as a post. Likewise, the pulley element 72 is mounted to the tool base segment 62 via a similar post. In some embodiments, The tool element 80 is mounted or coupled to the pulley element 70 via a mechanical interference connection so as to minimize backlash and form a tighter connection, such as for example by an interlocking arrangement as shown in FIGS. 5, 7A-7D, 9, and 10A-10C. Similarly, the tool element 82 is mounted to the pulley element 72 via a similar arrangement. The assembled tool base with tool elements 80, 82 is shown in FIG. 6. Each of the tool base segments 10, 62 can include a connecting flange 64, 66, respectively, each of which has an opening formed therein. The opening can be coupled to a suitable connector formed at an end portion of the robot arm 42.

As illustrated, the tool base portion 56 can include two independently driven, rotating pulley elements 70, 72. When the pulley elements are disposed so as to open the tool elements into a wider angle than is needed in surgery (e.g., an open tool exchange position), mechanical features on the pulley elements align and allow the tool elements to be easily removable therefrom, such as by sliding off, or by gently pushing the tool off of the tool base depending on the selected open geometry. Specifically, each of the rotatable pulley elements 70, 72 has a boss element formed thereon that is configured to engage with a complementarily shaped groove or cut-out formed in a corresponding tool element 80, 82. When a tool element is placed onto an empty tool exchange base, FIG. 11, the mechanical interface formed by the boss element of the pulley elements and the cut-out of the tool elements self-align with a funnel like slope (FIGS. 4 and 10) so as to be able to be precisely positioned within the base with a pin-like alignment. This funnel and pin combination shape allows for less accurate placement to always result in a tool element that self-secures or mounts within the tool base after any small driven movement away from the open tool exchange position. This accurate mechanical alignment may also align any needed electrical contacts, without any additional work or complexity, thus allowing the tool element to be immediately able to be actuated and used.

By using the same actuating motion that is used during normal tool movement to also release tools when the tool element (e.g., grasper) is hyper-extended into the open tool exchange position, the tool element interlock feature is added without requiring any additional actuation cables or motors. By having each tool element interlock in a mechanical manner, both sides of the tool can be oriented into a specific position so as to release the tool. Thus, the current tool mounting design allows the tool elements to still move across a full range of motion in a closed or partially-closed position, which are the positions surgeons need to use the tool during surgery.

Conventional surgical robotic systems require the associated arm or laparoscopic tool to be fully removed from the patient to be swapped out with another tool during surgery. The present invention allows for that swap to happen if desired within the patient, without requiring additional degrees of freedom in the arm or limiting the useable range of the tool. The tool swap can occur by inserting a tool introducer into the patient to deploy a suitable tool swapping instrument. According to another practice, the tool elements can be removed either by using the opposing robotic arm or by allowing the tool elements to slide off during tool removal. By moving the tool swap inside the patient, the surgical procedure may become faster, more automated, and less material intensive. Alternatively, the tool exchange or swap out can occur outside of the patient as well.

FIGS. 7A-7D illustrate the tool elements 80, 82 disposed in various positions relative to each other. For example, as shown in FIG. 7A, the tool elements 80, 82 can be positioned relative to each other into the open tool exchange position so that the mechanical features (e.g., slots or wedge elements) of the tool elements are aligned with the corresponding surface features (e.g., bosses) of the respective pulley elements 70, 72. When disposed in the open tool exchange position, the tool elements can be separated by a predetermined angular distance. According to one embodiment, the angular distance is about 180 degrees, although other or different angular distances can be used as well. The angular distance between the tool elements when disposed in the open tool exchange position preferably does not mimic or is similar to a normal or typical angular separation between the tool elements during surgical use. The tool elements 80, 82 can thus easily slide into the proper mounting position. FIGS. 7B and 7C show the mating features of the tool elements and the pulley elements during mounting. As the tool elements 80, 82 are slid or pushed downward onto the corresponding pulley elements 70, 72, the funnel-like mating of the slots and bosses automatically engage and align the tool elements into the initial open tool exchange position, as shown. FIG. 7D shows that when the tool elements 80, 82 start to move toward each other by the pulley elements, the tool elements lock into place due to the pin-like top alignment feature and the shared axle (e.g., post or pin) in the tool elements.

Figures 8A, 8B, 8C, 8D:
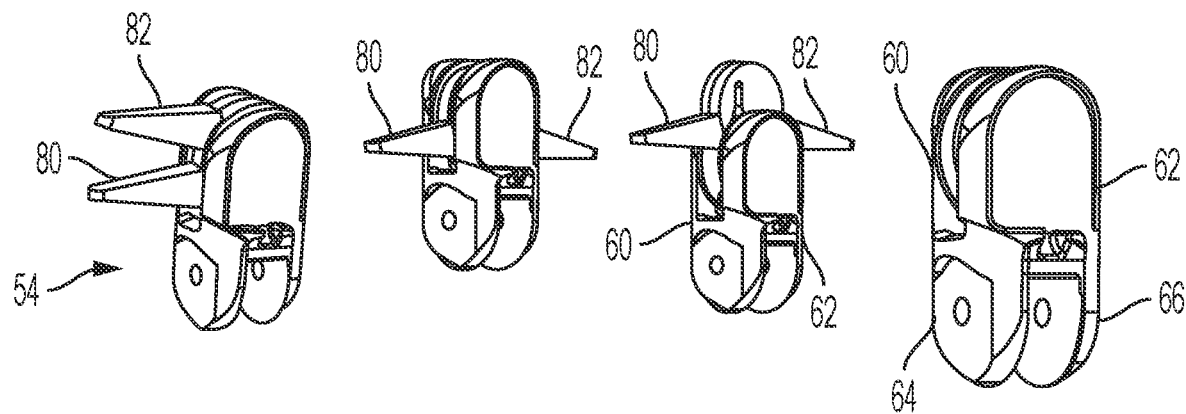
FIG. 8A is a perspective view of the end effector portion of the present invention showing the mounted tool elements in a selected position during use.
FIGS. 8B and 8C are perspective views of the end effector portion of the present invention showing the mounted tool elements in an open tool exchange position where the tool elements can be mounted on the tool base portion or removed therefrom.
FIG. 8D is a perspective view of the tool base portion of the present invention when assembled.
Figure 9:
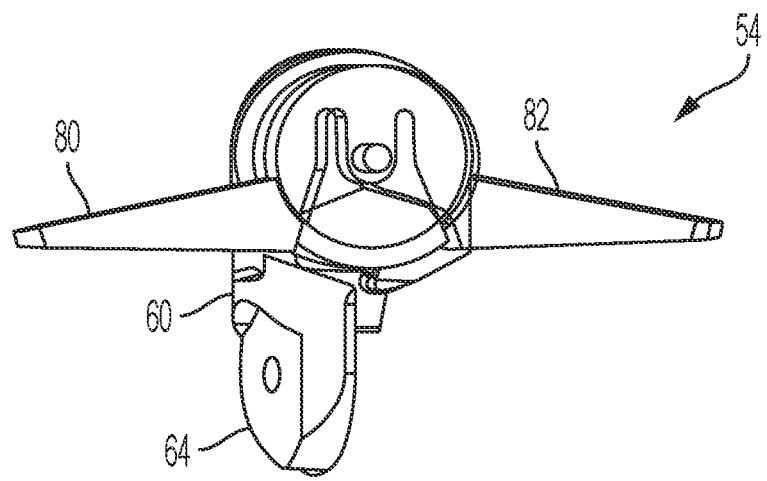
FIG. 9 is a partial perspective view of the end effector portion of the present invention showing the mounted tool elements in an open tool exchange position where the tool elements can be mounted on the tool base portion or removed therefrom.
Figures 10A, 10B, 10C:
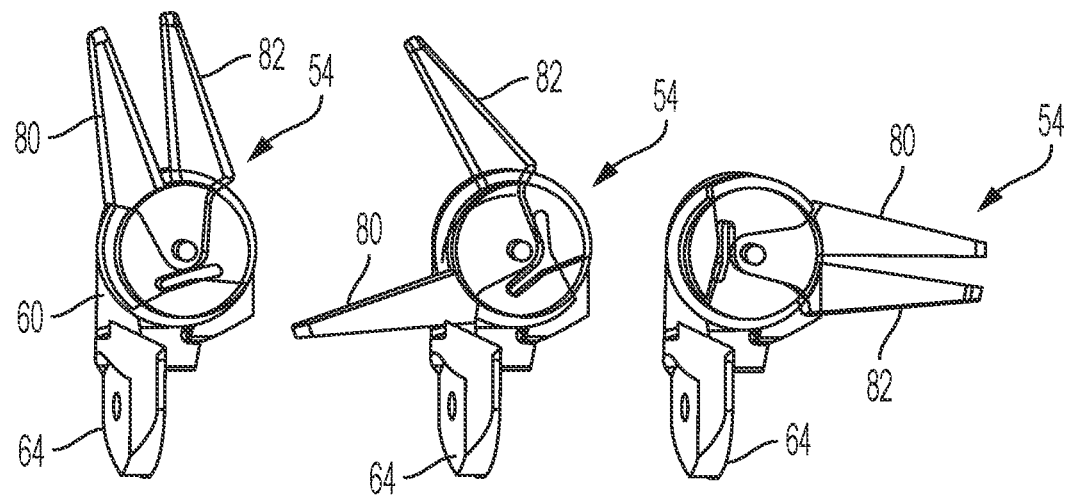
FIGS. 10A-10C are partial perspective views of the end effector portion of the present invention showing the mounted tool elements in selected positions during use.
Figure 11:
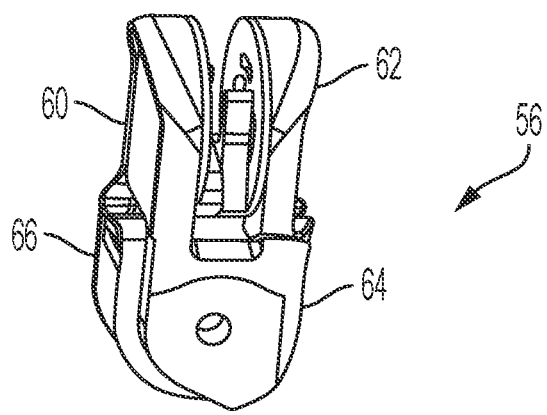
FIG. 11 is a perspective view of the tool base portion according to the teachings of the present invention.

FIGS. 8A-8D, 9, 10A-10C, and 11, show the movement and operation of the tool elements 80, 82 during use of the end effector segments as part of the robotic arm 42 of the present invention. Specifically, FIGS. 8A and 10A-10C show the tool elements 80, 82 in one of many various operational positions, where the tool elements 80, 82, shown as graspers, are locked into the tool base portion 56 and can be used to grasp, pull or push any selected device or tissue within the patient during surgery as part of the robot arm. As shown in FIGS. 8B, 8C and 9, when a different tool element is needed to be attached to the tool base, the pulley elements can drive the tool elements into the fully open tool exchange position (FIG. 7A) so as to allow or enable the tool elements to be removed from the base. As noted above, the tool exchange can occur within the patient by using a separate tool instrument positioned in the patient by a tool introducer or by using the opposing robotic arm. When properly configured, such as shown in FIGS. 7B and 8B, the tool elements 80, 82 can be removed by simply lifting up the elements relative to the base, and the tool elements can be stored in the surgical site or removed from the patient as desired. FIGS. 8D and 11 illustrate the tool base when the tool elements are removed or prior to installation of the tool elements. As such, the tool base portion 56 is ready to accept a tool element therein.

FIGS. 12A-12C show the actuation mechanism associated with the pulley elements 70, 72 of the tool base portion 56 for moving the tool elements 80, 82. As shown, a single pulley element which is driven by an actuation mechanism, which can include a pair of cables 90, 92. The cables 90, 92 enter the pulley from the bottom, wrap around selected portions of the pulley in order to actuate it, and then continue to wrap in the inside of the pulley to create more friction. Finally, the cables each terminate in a knot or in some other manner (as shown by the increased diameter region) and any remaining tail is tucked into a pocket. FIG. 12B shows the other side of the pulley of FIG. 12A. FIG. 12C shows the tool base portion 56 with all four driving cables—an opposing pair on each side and coupled to the respective pulley element.

Figures 13A, 13B:
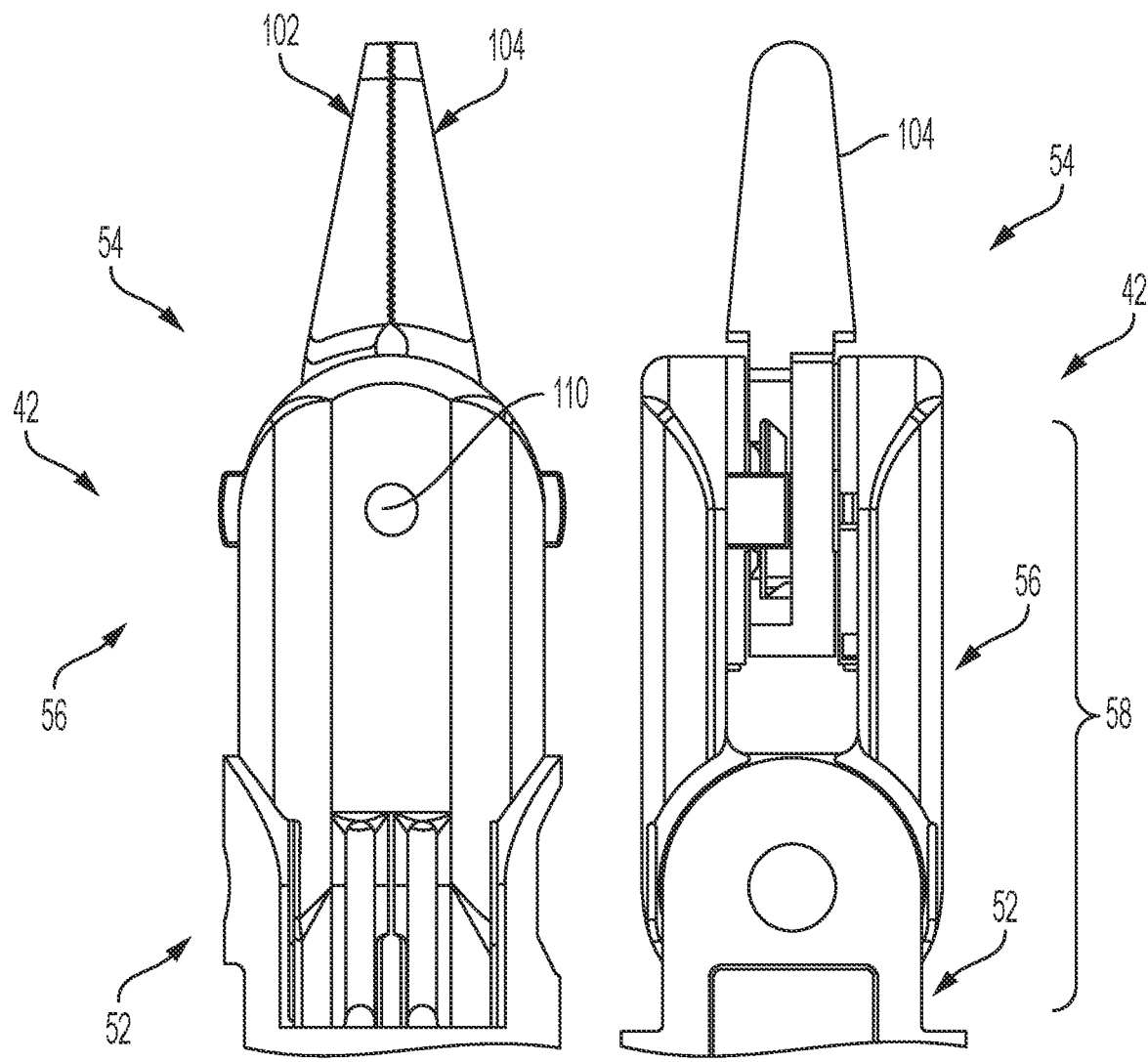
FIG. 13A is a side perspective view of the end effector portion of the robot arm according to a second embodiment of the present invention.
FIG. 13B is a front perspective view of the end effector portion of the robot arm of FIG. 13A according to the teachings of the present invention.

FIGS. 13A and 13B illustrate the general design of selected components of a robot arm 42 of the surgical robotic unit 50 according to a second embodiment of the present invention. Like reference numerals indicate like parts throughout the various views. For the sake of simplicity, only a single robot arm is shown, although a second robot arm or subsequent robot arms can be similar or identical in form and function. Similar to the foregoing embodiments, the robot arm 42 can include a series of articulation segments 52 that form joint sections that correspond to the joints of a human arm. As such, the articulation segments 52 can be constructed and combined to provide for rotational and/or hinged movement so as to emulate different portions of the human arm, such as for example the shoulder joint or region, elbow joint or region, and the wrist joint or region 58. The articulation segments of the robot arm 42 are constructed to provide cable-driven, rotational movement, for example, but within the confines of reasonable rotational limits. The articulation segments are configured to provide maximum torque and speed with minimum size. The articulation segments can be mechanically coupled together and end in an end effector portion or segment 54. The end effector portion 54 includes a tool base portion 56 that can incorporate therein any selected surgical tool to be employed so as to perform a desired or selected surgery. For example, the tool base portion 56 mounts a pair of tool elements 102, 104. In the current example, the tool elements are grippers or graspers, although those of ordinary skill in the art will readily recognize that any selected type of surgical tool can be employed. As shown in FIG. 13B, the end effector portion 54 and the adjacent arm segment 52 form a wrist portion or joint 58 of the robot arm. The end effector portion 54 is shown in detail for example in FIGS. 14A-26B.

Figure 14B:
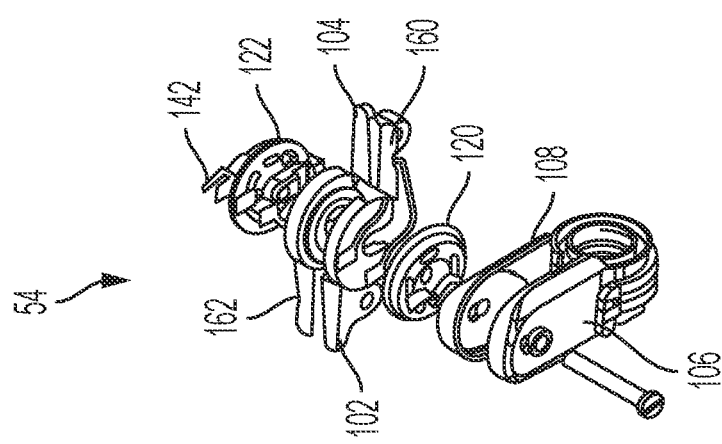
FIGS. 14A through 14E are exploded views of the end effector portion according to the teachings of the present invention.
Figure 14A:
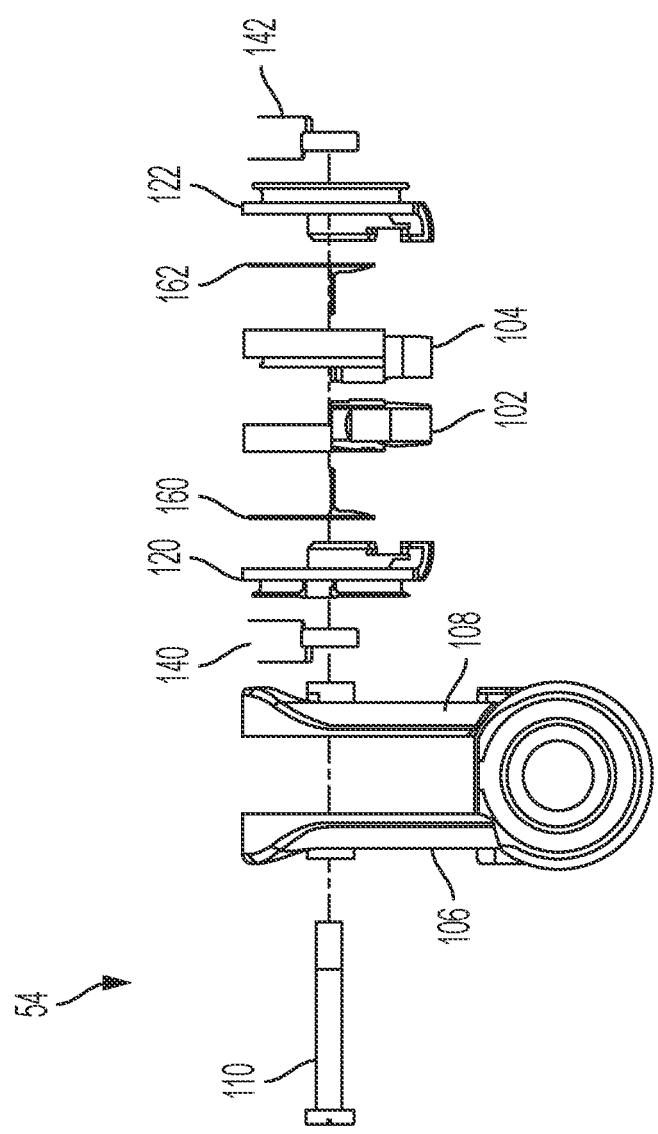
Figure 14C:
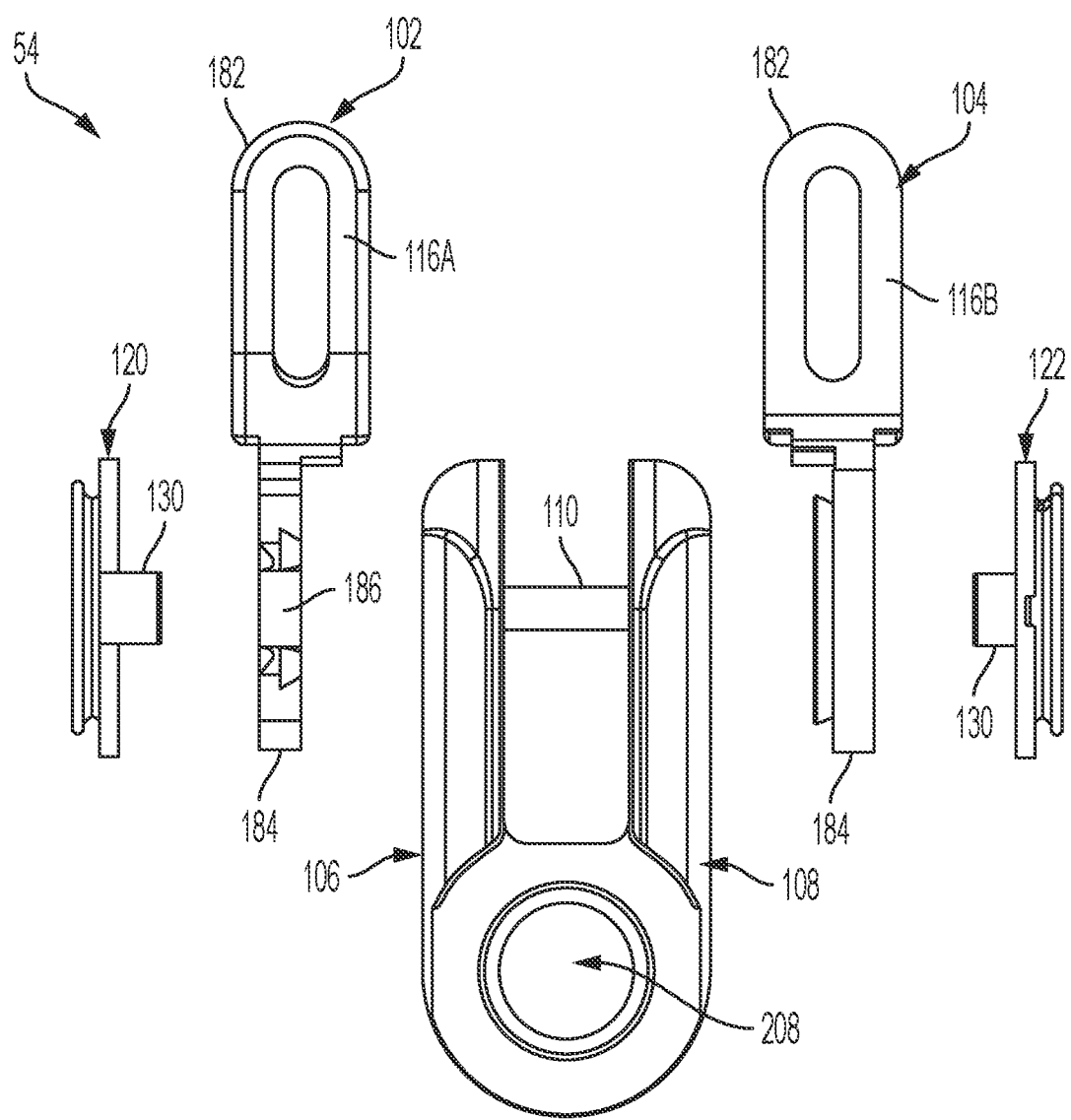
Figure 14D:
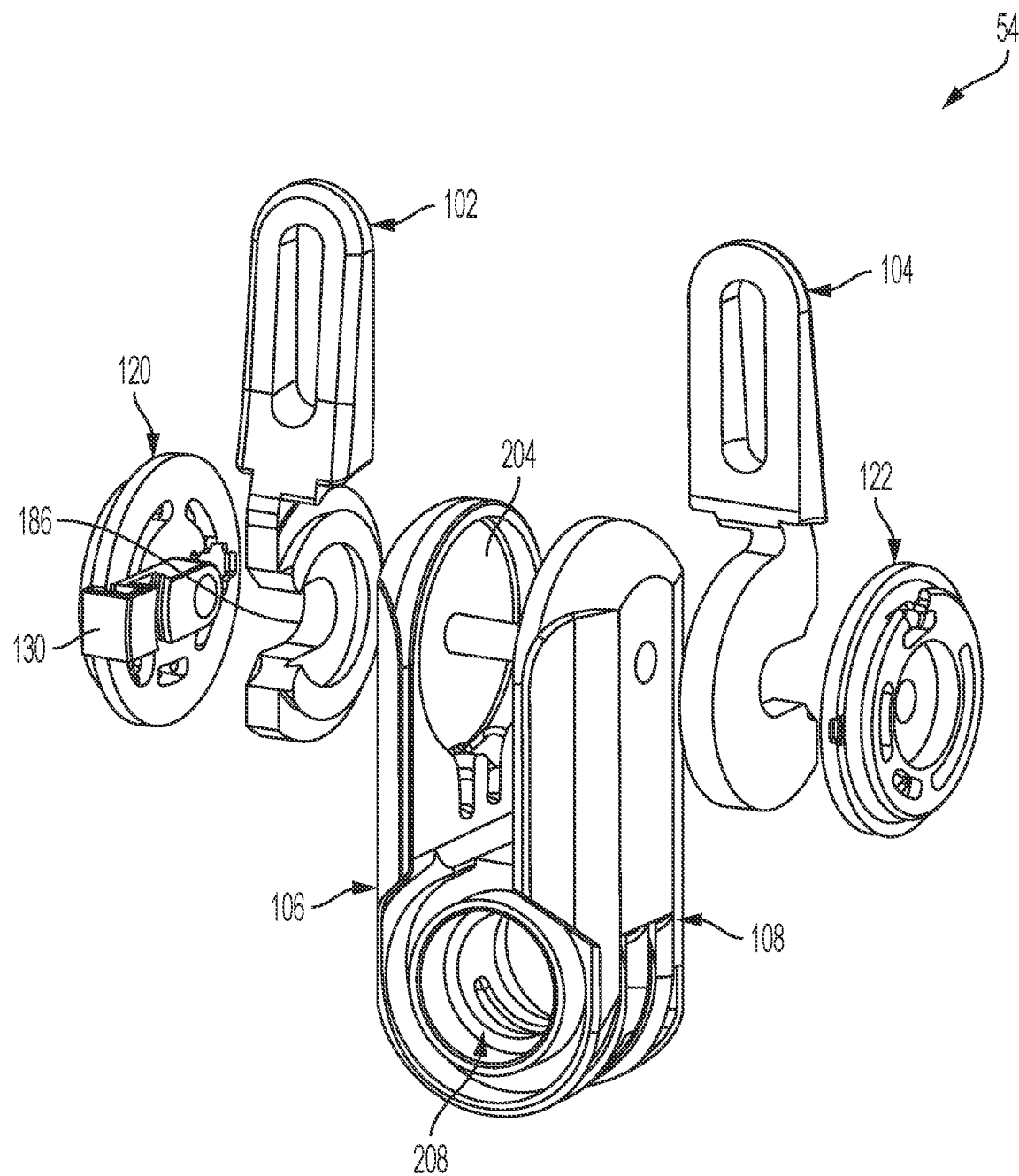
Figure 14E:
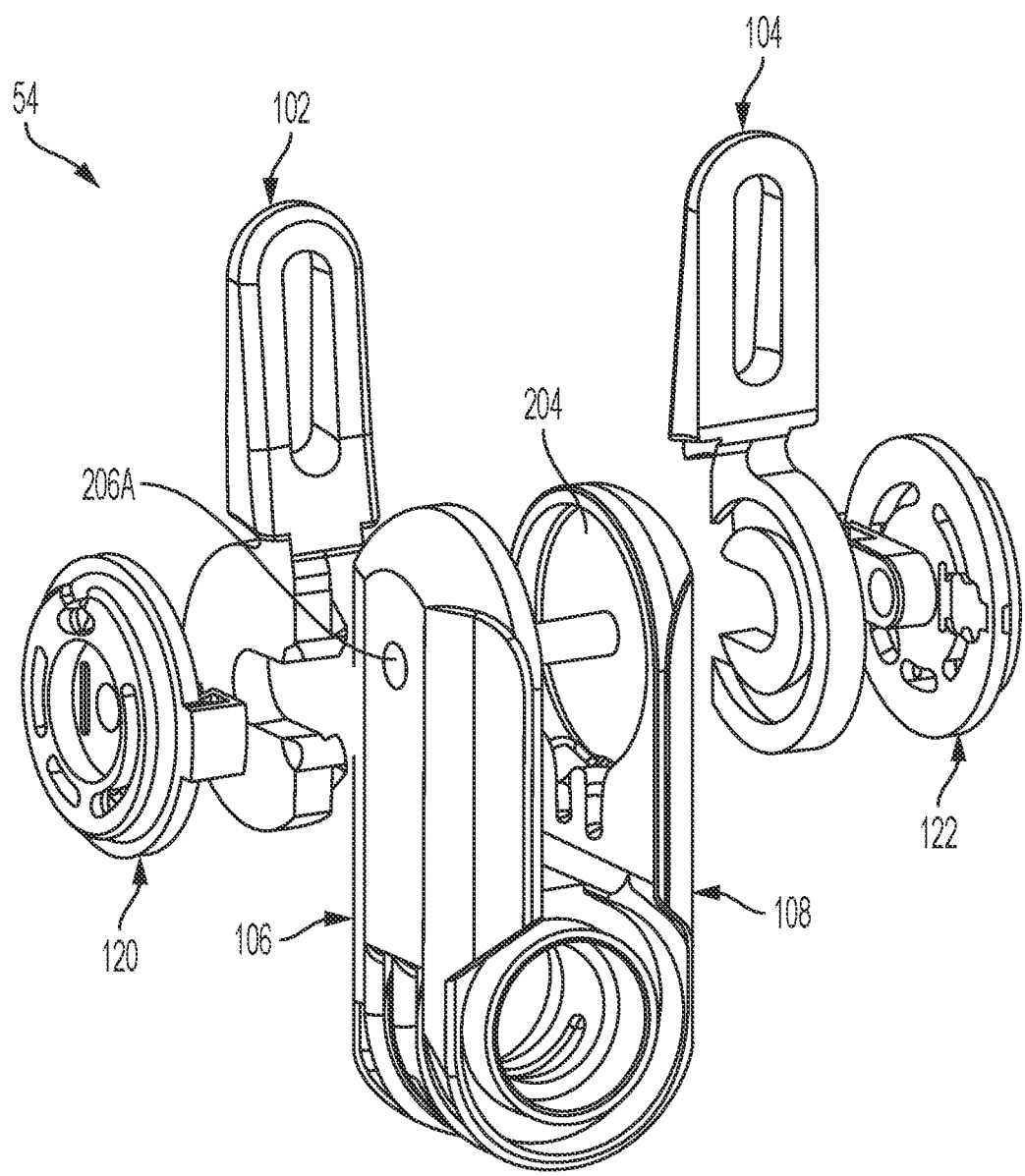

FIGS. 14A and 14B are exploded views of the end effector portion 54 of the robot arm 42 according to the teachings of the present invention. The illustrated end effector portion 54 includes a tool base portion 54 that includes a pair of tool base segments 106, 108 that can be connected together via a shaft or axle element 110. The axle element can be formed from any selected material, and is preferably formed from non-conductive material, such as ceramic. The end effector portion 54 also includes a pair of pulley elements 120, 122 that are coupled to the tool base segments 106, 108, respectively. The end effector portion 54 further includes a pair of conductive spring elements for coupling electrosurgical energy to the tool elements 102, 104 via a pair of conductive contact elements 160, 162. The conductive contact elements 160, 162 are coupled to the tool elements 102, 104, respectively.

Figure 15:
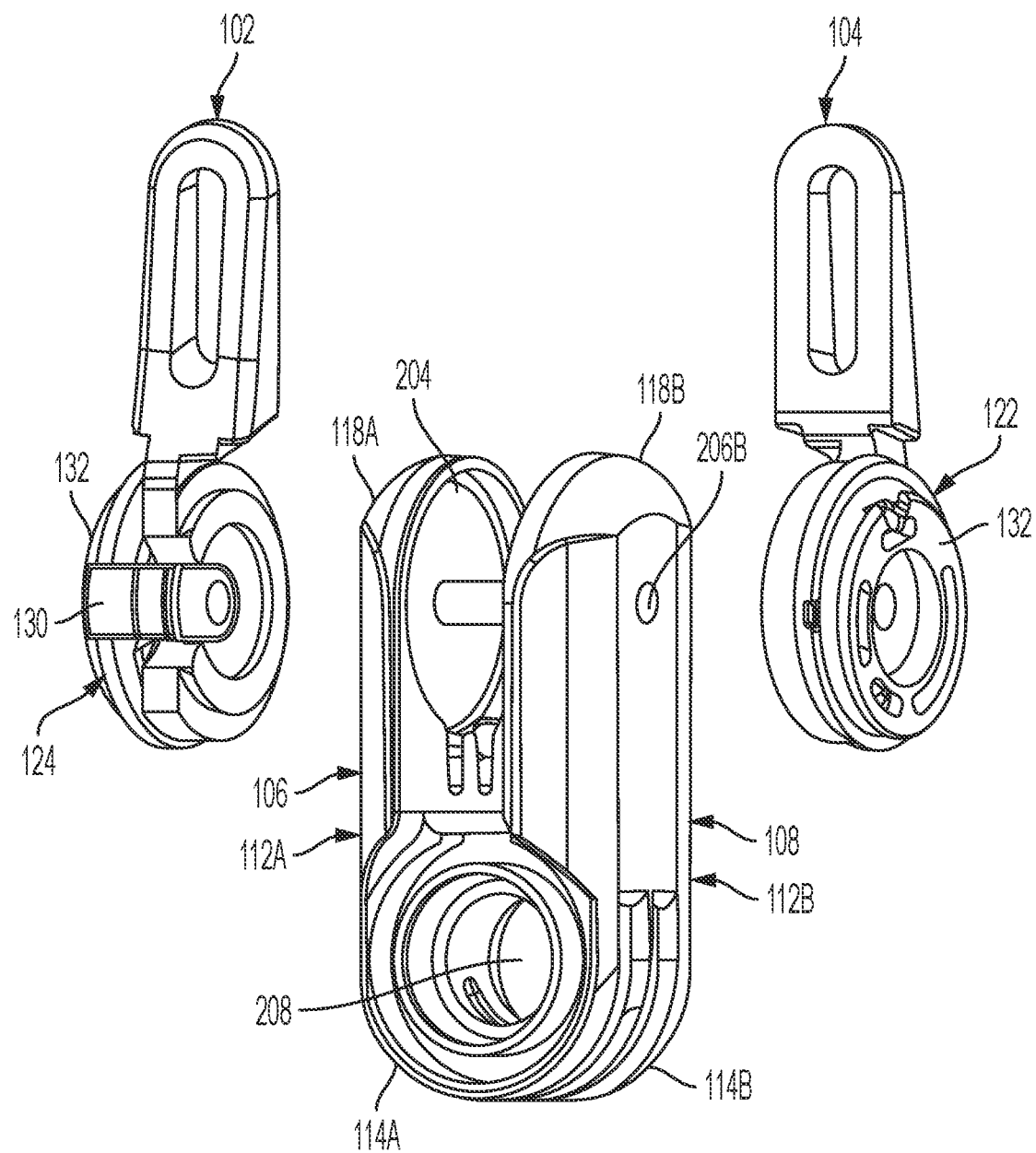
FIG. 15 is an exploded perspective view of the end effector portion according to the teachings of the present invention.
Figure 17A:
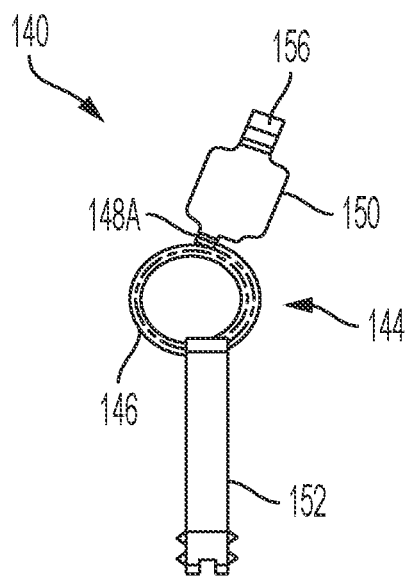
FIG. 17A is a front view of a conductive spring element of the end effector portion according to the teachings of the present invention.
Figure 17B:
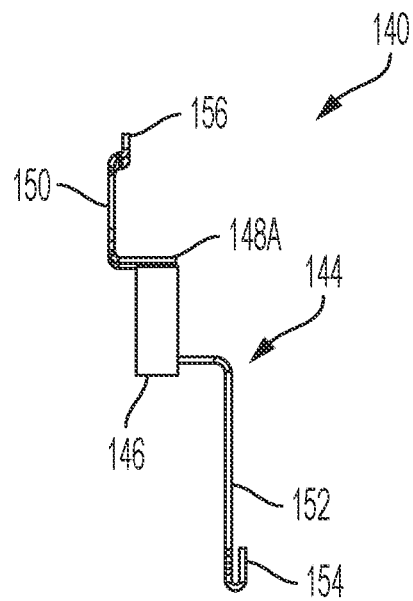
FIG. 17B is a side view of the conductive spring element of the end effector portion according to the teachings of the present invention.
Figure 17C:
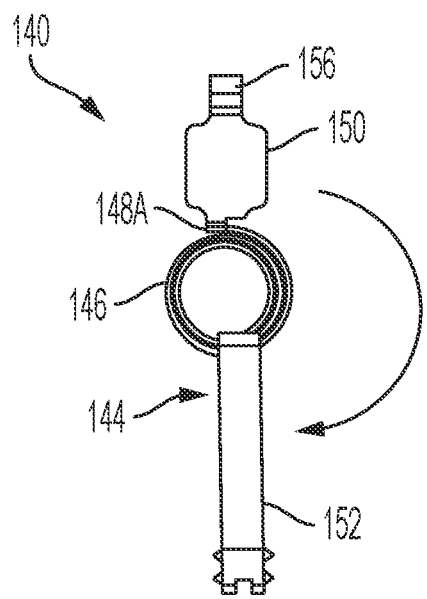
FIG. 17C is a front view of the conductive spring element in a first exemplary operational position according to the teachings of the present invention.
Figure 17D:
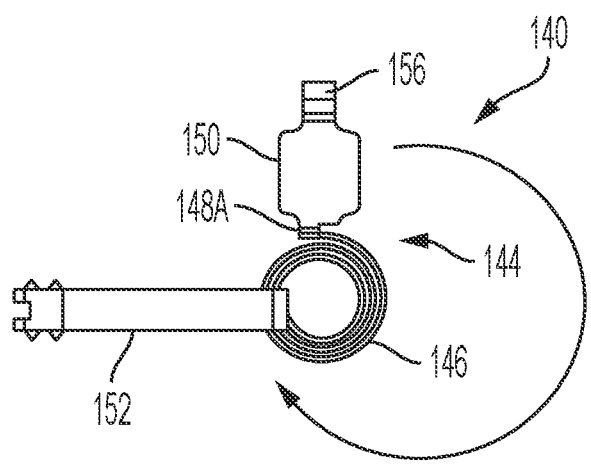
FIG. 17D is a front view of the conductive spring element in a second exemplary operational position according to the teachings of the present invention.
Figure 18A:
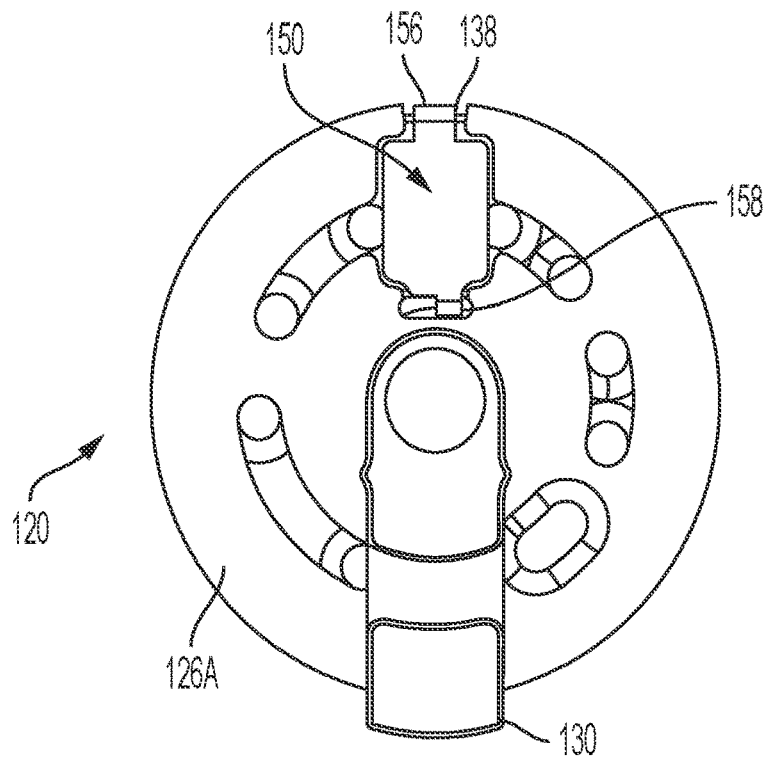
FIG. 18A is a front view of the pulley element with the conductive spring element coupled thereto according to the teachings of the present invention.
Figure 18B:
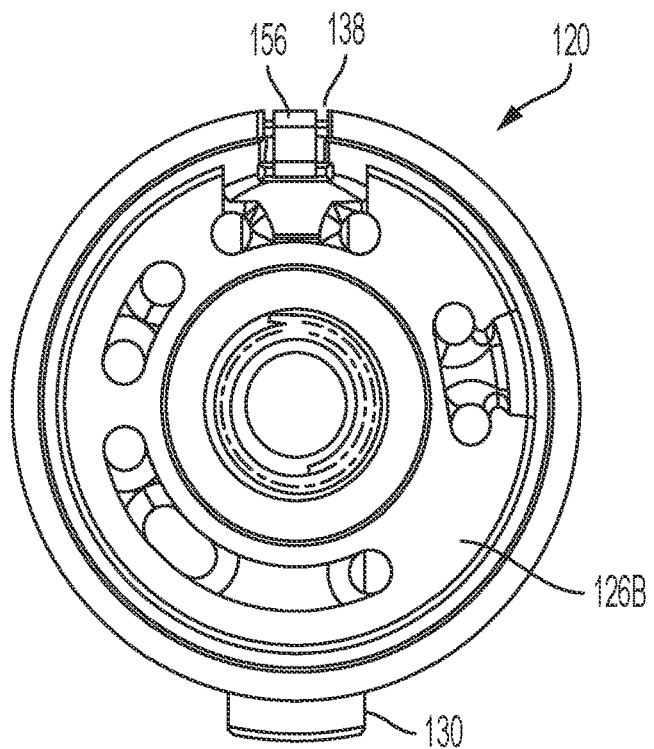
FIG. 18B is a rear view of the pulley element with the conductive spring element coupled thereto according to the teachings of the present invention.
Figure 19B:
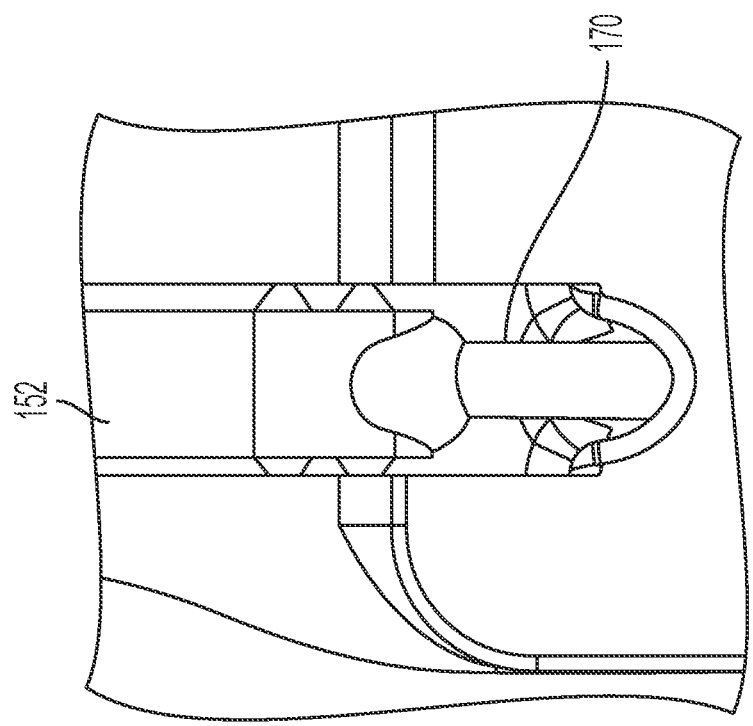
FIG. 19B is a close-up, partial cut away view of the of the end effector portion of the robot arm illustrating the connection of the conductive spring element and the internal electrical wire according to the teachings of the present invention.
Figure 19A:
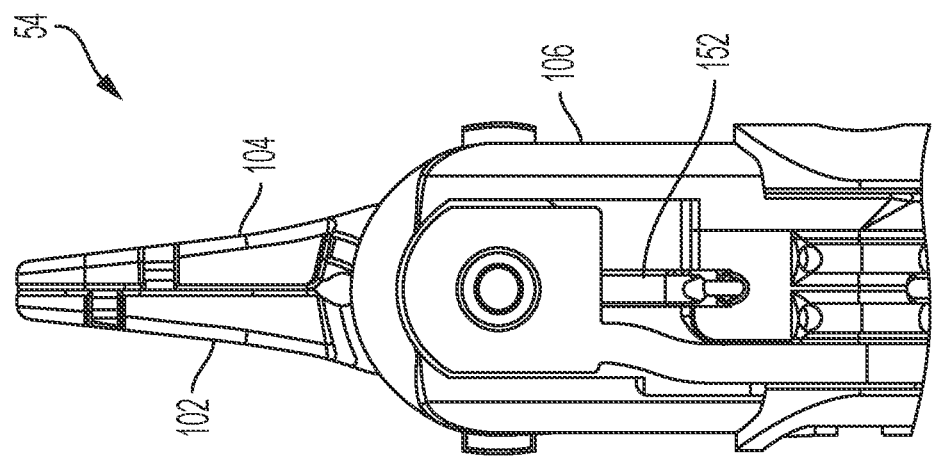
FIG. 19A is a partial cut away view of the end effector portion of the robot arm illustrating the connection of the conductive spring element and an internal electrical wire according to the teachings of the present invention.
Figures 20A, 20B:
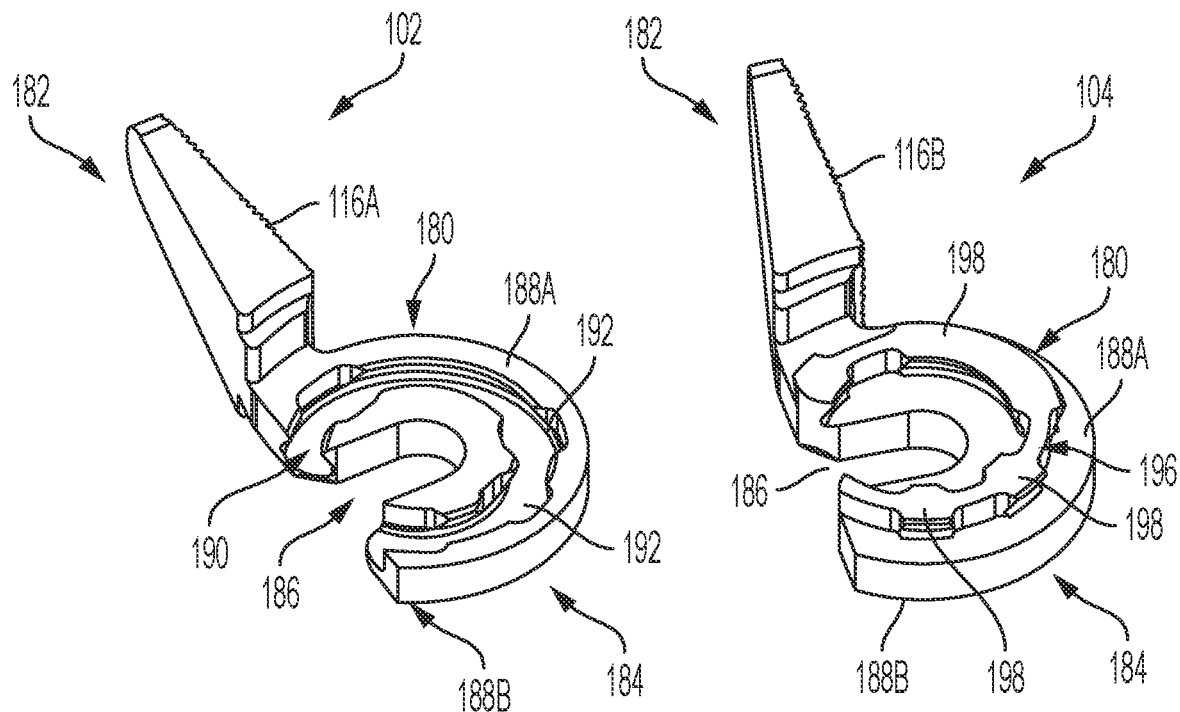
FIGS. 20A and 20B are front side perspective views of the tool elements of the present invention showing the mating surface features for coupling the tool elements together.

As illustrated in FIG. 15, the illustrated tool base portion 56 includes the opposed pair of tool base segments 106, 108. Each of the tool base segments includes a main body 112A, 112B that includes a flange portion 114A, 114B that can be configured to be coupled to an adjacent arm segment 52 of the robot arm 42. The main body an extension portion 118A, 118B that extends upwardly from the respective flange portions 114A, 114B. Each of the flange portions has a recess 204 formed therein for receiving a corresponding portion of the pulley elements 120, 122. Specifically, the connection element 132 of the pulley elements 120, 122 seat within the recess 204. The extension portion 118A, 118B also include an aperture 206A, 206B, respectively, for receiving and seating the axle element 110. Further, the flange portions 114A, 114B have an opening 208 formed therein for connection to the terminal end portion of the robot arm.

FIGS. 16A-16C illustrate the pulley element 120 of the end effector portion 54 of the present invention. For the sake of simplicity, we describe herein only pulley element 120, since the pulley element 122 has identical features. The pulley element 120 has a main body 124 that has an inner surface 126A and an opposed outer surface 126B. The main body 124 has a central aperture 128 for seating the axle element 110, as well as a plurality of holes 136 for seating a portion of a respective cable 90, 92 for controlling the circular or rotational movement of the pulley element. The holes 136 can have the same or different shapes and can have different sizes. The inner surface 126A has a surface feature formed thereon, and is preferably a raised or protruding boss element 130. The boss element 130 can have any selected shape or configuration and can have any selected size. The boss element 130 preferably is shaped in a manner complementary to a receiving portion of one of the tool elements, as described herein. The outer surface 126B of the pulley element also has a surface feature formed thereon, and is preferably formed as a raised or protruding connection element 132. The connection element 132 can have any selected shape or size, and preferably has a round or circular shape. The connection element 132 can include a narrower base portion that is coupled to the outer surface 126B so as to form a groove 134. The groove 134 is configured for receiving a portion of the distal end of the cables 90, 92, so as to store the distal end portion of the cable during use. The connection element 132 is adapted to seat within the main body 204. The main body 124 also includes a slot 138 that is configured for seating a portion of the conductive spring element 140 so as to secure the spring element thereto. The pulley elements 120, 122 are cable driven components that can control, based on the cable position, the orientation or rotational position of the tool elements 102, 104.

The conductive spring element 140 is shown for example in FIG. 17A-19B. For the sake of simplicity, we describe herein only conductive spring element 140, since the conductive spring element 142 has identical features. The illustrated conductive spring element 140 has a main body 144 that has a central coil element 146 that has one coil end 148A coupled to a top tab portion 150 and an opposed coil end 148B coupled to an opposed or bottom tab portion 152. The central coil element 146 is expandable and retractable based on the position of one or more of the tab portions. The bottom tab portion 152 has a bent end portion 154, FIG. 17B. The top tab portion 150 includes a connection element 156 for coupling to the pulley element 120. The central coil element 146 seats within a central portion of the outer surface 126B of the pulley element 120, FIG. 18B, and the top tab portion 150 passes through a central slot 158 formed in the main body 124 of the pulley element 120 to the inner surface 126A of the pulley element. The tab portion 150 then passes along the inner surface 126A until the connection element 156 seats within the slot 138. The bent portion 154 of the bottom tab portion 152 contacts and connects to a portion of the tool base segment 106. The bottom tab portion 152 is also connected to a terminal end of a power supply wire 170 that passes through the robot arm 42 to the wrist portion 58. The tab portion 152 can be fastened to the wire 170 by any known means, such as for example by soldering or by known wire connectors. The bottom tab portion 152 is thus disposed in a fixed position relative to the main body 204. The tab portion 150 rotates with the pulley element 120. Further, when the boss element 130 is disposed in the open tool exchange position, as shown for example in FIGS. 16A and 18A, the tool element 102 can be slid on and off the boss element 130. In this position, the top tab portion and the bottom tab portion 152 are oriented in opposite directions, and are disposed about 180 degrees apart, as shown in FIG. 17C. When the pulley element 120 is rotated by the cables 90, 92 away from the open tool exchange position, the top tab portion 150 moves relative to the fixed bottom tab portion 152. When the pulley element 120 and hence the boss element 130 is rotated about 90 degrees from the open tool exchange position, then the top tab portion 152 is rotated as well a further 90 degrees and is disposed at a right angle relative to the bottom tab portion 152, as shown in FIG. 17D. The conductive spring element 140 can be made of any electrically conductive material, such as for example metal. The conductive spring element 140 allows for the electrical connection or communication of different types of electrical energy (e.g., monopolar and bipolar electrical energy) to the tool elements, such as during electrosurgery and electrocautery type procedures.

The illustrated tool elements 102, 104 are shown in further detail in FIGS. 20A-25. The illustrated tool elements can have any selected shape and size, and can include, for example, graspers or grippers, suture device, scissors, and the like. The illustrated tool elements 102, 104 are configured to be connected to form a combined surgical tool. The tool element 102, for example, includes a main body 180 that has an engagement end 182 for engaging with another device or tissue, and a securing end 184 for securing the tool element 102 to a corresponding pulley element, such as for example with the pulley element 120. The engagement end 182 can include any selected type of surface and provide any selected type of functionality based on the intended use and purpose of the tool. For example, in the current example, the graspers can include a knurled or serrated working surface 116A to enhance the grasping capabilities of the tool. Further, the engagement end 182 can optionally mount the conductive contact element 160 for providing surgical energy to the surgical site, if desired. The securing end 184 includes a surface feature formed therein, such as for example a slot 186 that is complementary in shape to the boss element 130 formed on the inner surface 126A of the pulley element 120. The connection and mating engagement of the slot 186 and the boss element 130 rotationally secures the tool element 102 to the pulley element 120. The tool elements 102, 104 can be secured or coupled together by any selected connection technique, and preferably are coupled together using a dovetail joint configuration. The dovetail joint secures the tool elements 102, 104 together in such a manner that it is difficult to pull the tool elements apart, since the joint has a relatively high tensile strength. For example, the tool element 102 has a surface feature formed on a first inner facing surface 188A of the securing end 184. The securing end 184 also includes an opposed outer facing surface 188B. The surface feature can include for example a groove or socket 190 that is sized and configured for receiving a rail or tail portion. The groove 190 has an undercut configuration so as to properly seat the corresponding rail portion. The groove 190 also includes one or more widened sections 192 that seat a corresponding portion of the rail portion.

Figure 22A:
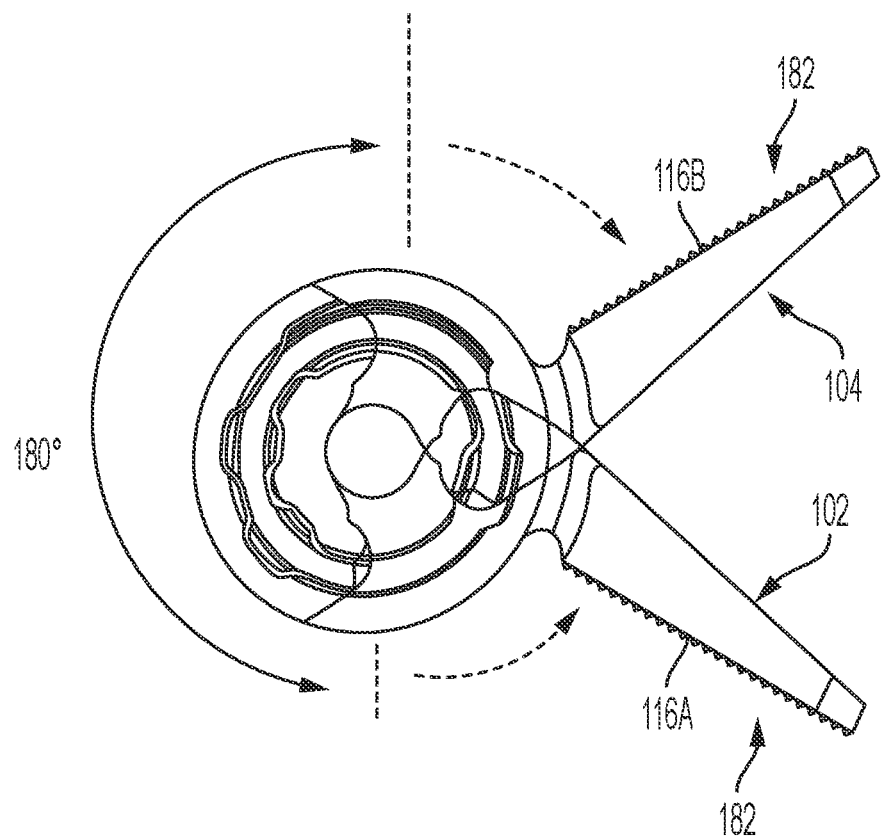
FIGS. 22A and 22B are perspective views of the tool elements when coupled together according to the teachings of the present invention.
Figure 22B:
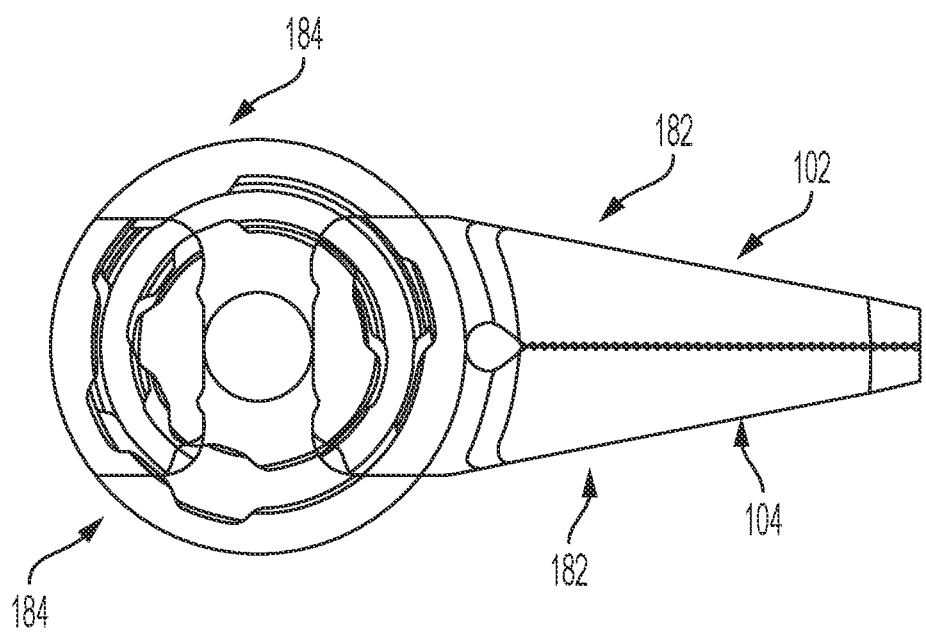

Similarly, the tool element 104 includes a main body 180 that has an engagement end 182 for engaging with another device or tissue at the surgical site, and an opposed securing end 184 for securing the tool element 104 to a corresponding pulley element, such as for example to the pulley element 122. The securing end 184 also has a surface feature formed therein, such as for example a slot 186 that is complementary in shape to the boss element 130 formed on the inner surface 126A of the pulley element 122. The connection and mating engagement of the slot 186 and the boss element 130 rotationally secures the tool element 104 to the pulley element 122. The illustrated tool element 104 also has a surface feature formed on a first inner facing surface 188A of the securing end 184. The surface feature can include for example a rail or tail portion 196 that is sized and configured for seating in the groove 190. The rail portion 196 also includes one or more widened portions or sections 198 that are complementary in shape and size to the widened sections 192 of the groove 190. As shown in FIGS. 22A and 22B, the tool elements 102 and 104 can be secured together by aligning the widened sections 192 of the groove 190 with the widened sections 198 of the rail 196. In this initial configuration, the engagement ends 182, 182 are disposed relative to each other such that they form an angle greater than 180 degrees, as shown. This initial position of the engagement ends dispose them well past the open tool exchange position of 180 degrees, and as such, the tool elements 102, 104 are secured to each other. When aligned, the rail 196 can be inserted into the groove 190 and then rotated so as to move the widened sections 198 into the groove 190. For example, the tool engagement ends 182, 182 can be moved into a normally closed position, as shown in FIG. 22B.

Figure 23A:
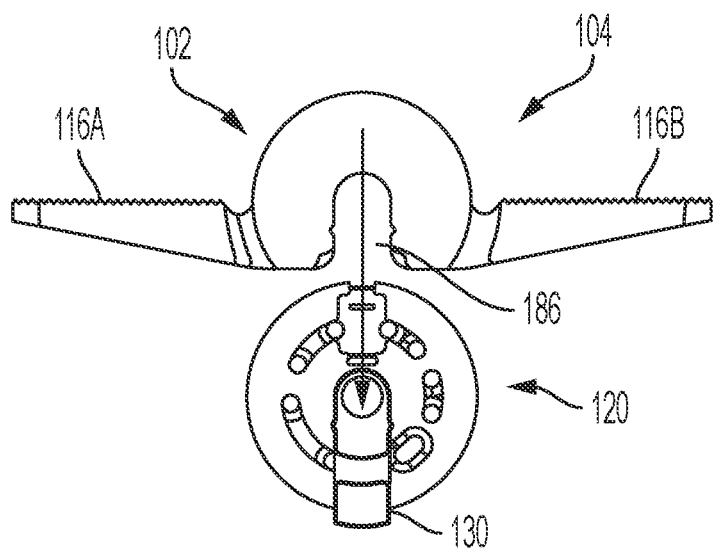
FIG. 23A is a front perspective view of the tool elements when mounted to a boss element of the pulley element according to the teachings of the present invention.
Figure 23B:
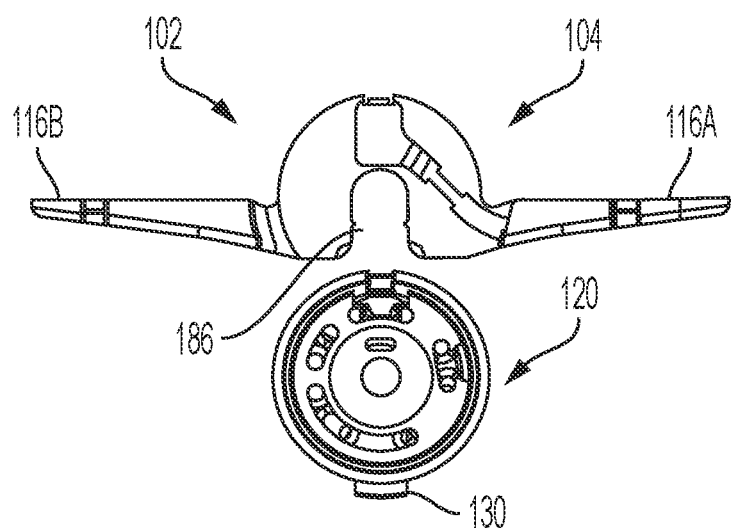
FIG. 23B is a rear perspective view of the tool elements when mounted to a boss element of the pulley element according to the teachings of the present invention.
Figure 23C:
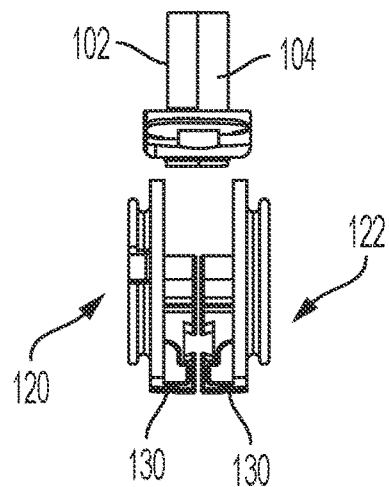
FIG. 23C is a side view of the tool elements when mounted to a boss element of the pulley element according to the teachings of the present invention

FIGS. 23A-25 show the mounting of the tool elements 102, 104 on the pulley elements, such as for example on the pulley element 120. FIGS. 23A-23C show the positioning of the tool elements 102, 104 relative to the boss element 130 of the pulley element 120, such that the slot 186 is aligned with the boss element 130, and then the tool elements 102, 104 are slid into a mounting or engagement position. Similarly, FIGS. 24A and 24B show the conductive contact element 160 secured to the tool element 102 by known techniques. For example, the conductive contact element 160 can be secured by solder, glue, or by mechanical fastening techniques, such as by crimping, to the tool element. The slot 186 formed in the securing end 184 is aligned with the boss element 130, and then the tool element 102 is slid or pressed into a mounting or engagement position. In the engagement position, a contact portion 164 of the conductive contact element 160 is placed in electrical contact with the top tab portion 150 of the conductive spring element 140. Further, the axle element 110 locks or secures together the various components of the end effector portion 56. When the tool element is removed from the boss element, the tab portion 150 and the contact portion 164 are frictionally engaged and serve to clean the respective contact surfaces.

In assembly, the cables 90 and 92 are connected to each of the pulley elements 120 and 122. The cable elements 90, 92 help move each of the pulley elements in any selected rotational direction. As such, the boss element 130 formed on the inner surface 126A of the pulley element is in turn rotated in opposed rotational directions. The tool base portion 56 of the end effector portion 54 can be assembled by pressing the connection element 132 of the pulley element 120 into a corresponding recess formed along an inner surface of the tool base segment 106. Likewise, the connection element 132 of the pulley element 122 can be pressed into a corresponding recess formed along the inner surface of the tool base segment 108. The tool elements 102, 104 can be coupled together by disposing the rail 196 into the groove 190 of the tool elements so as to form a dovetail joint. The tool elements can be coupled together using other known connection methods that provide both axial and radial mechanical constraints on movement of the tool elements relative to each other. The engagement ends 182, 182 of the tool elements 102, 104 can be positioned so that they are separated about 180 degrees apart into the open tool exchange position. In this position, the slots 186, 186 are aligned. The boss elements 130 of the pulley elements 120, 122 can also be aligned and positioned so as to seat in the slots 186, 186 of the tool elements when disposed in the open tool exchange position. This position is the maximum angular distance or separation between the engagement ends 182, 182 of the tool elements that is permitted during use. The cables 90, 92 can be actuated so as to independently rotate each pulley element 120, 122. The engagement ends 182, 182 of the tool elements can be individually or separately moved into subsequent rotational positions such that the engagement ends relative to each other are separated by an angle less than the 180 degrees position of the tool elements when disposed in the open tool exchange position. As such, each pulley element moves the respective tool element mounted thereon. For example, the pulley element 120 rotates or moves the tool element 102 and the pulley element 122 rotates or moves the tool element 104. The pulley elements are thus cable driven components that control the rotational position or orientation of the tool elements. The tool base portion 56 can accept or release the tool elements 102, 104 only when the boss elements 130, 130 are similarly aligned, such as when disposed in the open exchange tool position. When the boss elements 130, 130 are moved out of alignment with each other, a vertically outwardly disposed moving force applied to the tool elements does not dislodge or remove the tool elements from the tool base portion 56, and hence from the pulley elements 120, 122.

Figure 21:
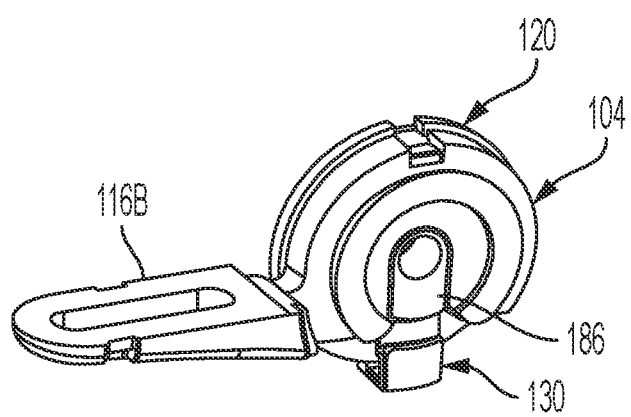
FIG. 21 is a perspective view of one of the tool elements mounted on a respective pulley element according to the teachings of the present invention.
Figures 24A, 24B:
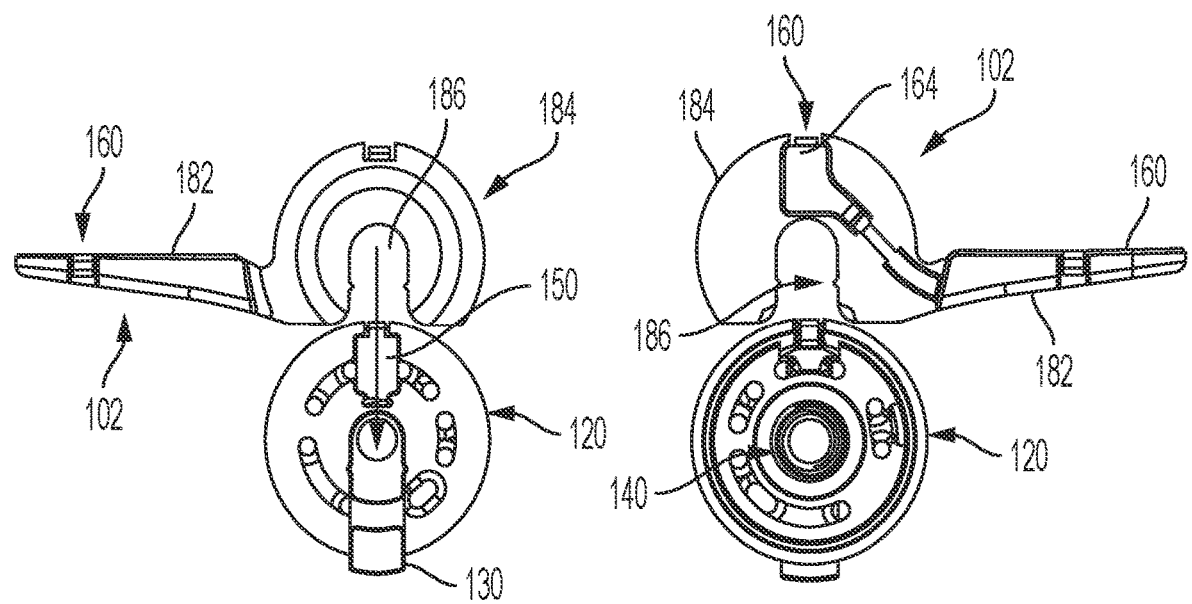
FIG. 24A is a front perspective view of a tool element and associated conductive contact element when mounted to the pulley element according to the teachings of the present invention.
FIG. 24B is a rear perspective view of a tool element and associated conductive contact element when mounted to the pulley element according to the teachings of the present invention.
Figure 25:
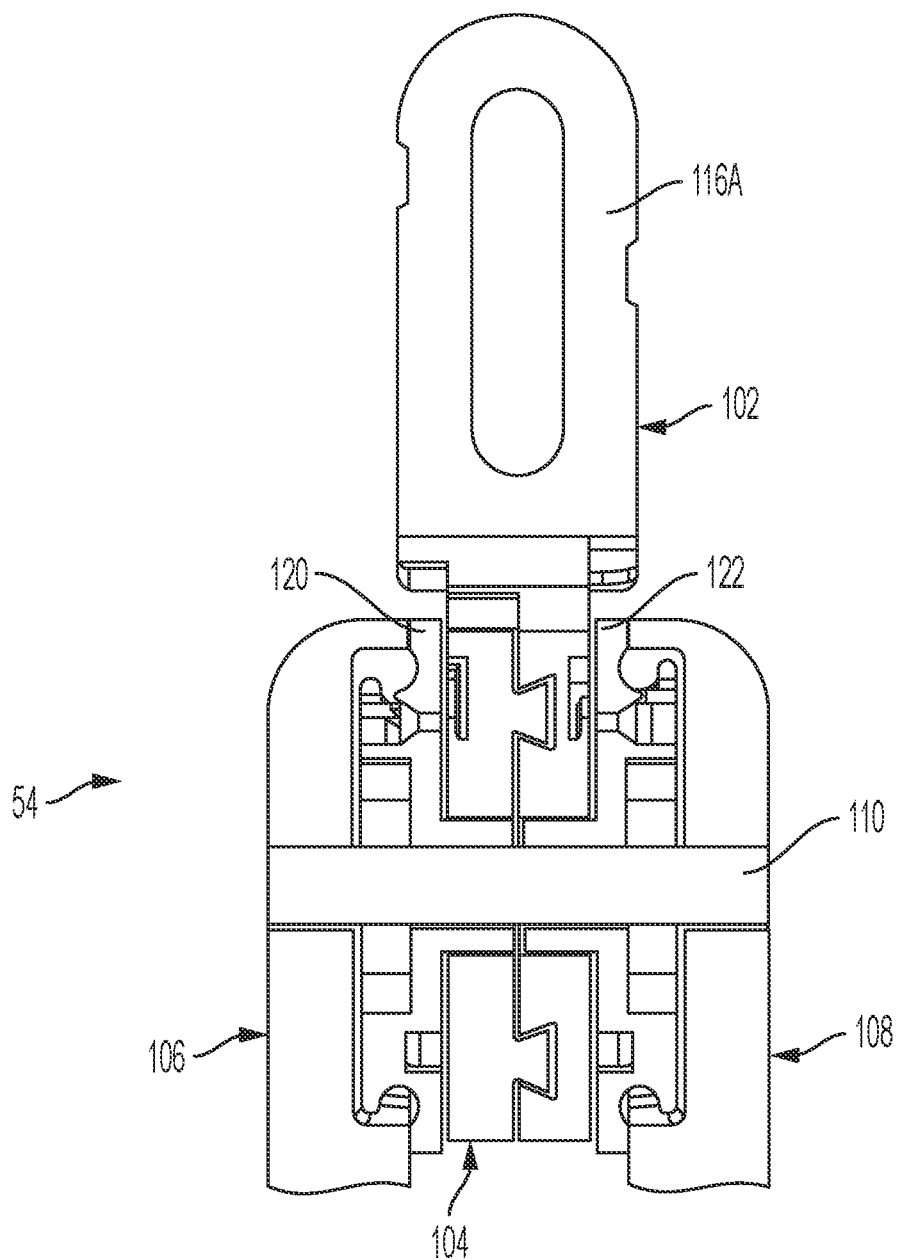
FIG. 25 is a side perspective view of the tool elements when mounted to the pulley elements of the present invention.

In operation, the robotic arm 42 can be equipped with a surgical tool, such as graspers, hooks, scissors, and the like, either within the patient or external to the patient. Regardless of the tool exchange location, the tool elements 102, 104 can be mounted or coupled to the tool base 56 by aligning the boss elements 130, 130 of the pulley elements 120, 122 in an aligned loading position and then aligning the slots 186, 186 of the tool elements. When the slots of the tool elements are aligned, in some embodiments the engagement ends 182, 182 of the tool elements are separated by a selected angular distance, such as for example about 180 degrees, thus placing the ends and hence the tool elements in the open tool exchange position. The angular distance can be any selected angular amount provided that it is not commonly used or achieved during surgical or regular use. The slots 186, 186 of the tool elements are then slid or pressed onto the bosses 130, 130 of the pulley elements 120, 122, as shown in FIGS. 21, 23A and 24A. The pulley elements 120, 122 can then be cable driven to move the tool elements 102, 104 into one or more surgical use positions, where the tool elements are separated by an angle less than 180 degrees. An example of one of many surgical use position is shown for example in FIGS. 26A and 26B, where the tool elements 102, 104 are separated by an angular amount or distance less than 180 degrees. Further, once one or more of the pulley elements 120, 122 rotate their corresponding boss element 130 away from the vertical loading position, as shown, then the tool elements 102, 104 are incapable of sliding off of or being removed from the boss elements and hence from the tool base 56.

Further, the conductive contact elements 160, 162 are connected to the tool elements 102, 104, respectively. The conductive contact elements are capable of conducting energy, such as electricity, to any material, such as for example tissue, or device that contacts any exposed portion of the conductive contact elements. The conductive contact elements preferably cover a selected portion of the working surfaces 116A, 116B of the tool elements 102, 104. For example, the working surfaces 116A, 116B of the tool elements can mount the conductive contact elements. The conductive contact elements are electrically coupled to the conductive spring elements via continual and persistent contact between the top tab portion 150 of the conductive spring elements 140, 142 and the contact portions 164, 164 of the conductive contact elements. The bottom tab portion 152 of the conductive spring elements 140, 142 is then disposed in contact with the power supply wire 170. The computing unit 18 can couple the power supply wire 170 to a monopolar power source that supplies relatively high voltage monopolar electrocautery energy or power to the conductive contact elements. Alternatively, the computing unit 18 can couple the power supply wire 170 to a bipolar energy source that supplies relatively high amperage bipolar electrocautery energy or power to the conductive contact elements.

The pulley elements 120, 122 can be independently driven and rotated by the cables 90, 92. As the boss elements of the pulley elements 120, 122 move from the loaded position, as shown in FIG. 22B, then the top tab portion 150 of the conductive spring element 140 moves relative to the stationary bottom tab portion 152. The central coil element 146 can expand and contract so as to allow or enable relative movement between the tab portions 150, 152 without damaging or destroying the conductive spring element. Further, the mounting arrangement of the tab elements forms a static electrosurgery connection between the top tab portion 150 and the conductive contact elements, as well as between the bottom tab portion 152 and the power supply wire 170, even as the tool elements are rotated between various rotational positions. This static mounting configuration reduces the risk of arcing between the contacts.

The ability of the pulley elements to be driven independently of each other provides for additional degrees of freedom in the current robot arms. Specifically, since each pulley element can be separately and independently driven by the cables, then the pulleys provide for an additional two degrees of freedom.

Those of ordinary skill in the art will readily recognize that the wrist portion or joint of the robot arms can be formed in different ways and thus have a different mechanical configuration. Specifically, the tool base portion of the robot arms can have any selected configuration. According to one alternate embodiment, the tool base portion of the robot arm can be configured to form a ball joint.

I claim:

1. A method for removing from and inserting on a wrist portion of a robot arm in a surgical robotic system one or more tool elements, comprising
   providing a tool base portion that is coupled to an end portion of the robot arm,
   rotatably coupling a first pulley element to the tool base portion,
   rotatably coupling a second pulley element to the tool base portion,
   securing the first and second pulley elements to the tool base portion with an axle element,
   providing a first tool element that can be coupled together with a second tool element, and
   configuring the first and second tool elements to be positioned into an open tool exchange position so as to be able to be mounted on or removed from the tool base portion.

2. The method of claim 1, further comprising configuring the tool base portion to include a first tool base segment and a second tool base segment,
   rotatably coupling the first pulley element to the first tool base segment, and
   rotatably coupling the second pulley element to the second tool base segment.

3. The method of claim 2, further comprising configuring the first and second tool elements to be removably and replaceably coupled to the tool base portion when disposed in the open tool exchange position.

4. The method of claim 2, further comprising
   configuring the first pulley element to have a first pulley surface feature formed thereon and configuring the second pulley element to have a second pulley surface feature formed thereon, and
   configuring the first tool element to have a first surface feature formed thereon that is complementary in shape to the first pulley surface feature of the first pulley element and configuring the second tool element to have a second surface feature formed thereon that is complementary in shape to the second pulley surface feature of the second pulley element,
   wherein when the first and second pulley surface features of the first and second pulley elements are aligned and when the first and second surface features of the first and second tool elements are aligned when disposed in the open tool exchange position, the first and second tool elements can be removably and replaceably mounted on the first and second pulley surface features of the first and second pulley elements, respectively.

5. The method of claim 4, wherein the step of providing a first tool element that can be coupled together with a second tool element further comprises
   configuring the first tool element to have a first connection surface feature formed thereon, and
   configuring the second tool element to have a second connection surface feature formed thereon that is complementary in shape to the first connection surface feature, such that the first and second connection surface features, when aligned, enable the first and second tool elements to be coupled together.

6. The method of claim 5, further comprising configuring the first connection surface feature to include a groove and configuring the second connection surface feature to include a protruding rail-like element.

7. The method of claim 5, further comprising configuring the first and second connection surface features to form a dove-tail joint connection.

8. The method of claim 5, further comprising, when the first tool element and the second tool element are assembled, locking the first and second tool elements together by selectively rotating one or more of the first and second tool elements out of the open tool exchange position and into one or more use positions by rotational movement of one or more of the first and second pulley elements.

9. The method of claim 5, further comprising
   providing a first conductive spring element that is coupled to the first pulley element and a second conductive spring element that is coupled to the second pulley element, and
   providing a first conductive contact element that is coupled to the first tool element and a second conductive contact element that is coupled to the second tool element.

10. The method of claim 9, further comprising maintaining direct contact between a portion of the conductive spring element and a portion of the conductive contact element, during use, and independent of a rotational position of the first and second pulley elements.

11. An end region device of a robot arm in a surgical robotic system, comprising
    a tool base portion that is coupled to an end portion of the robot arm by a connector,
    a first pulley element that is rotatably coupled to the tool base portion,
    a second pulley element that is rotatably coupled to the tool base portion, wherein the first and second pulley elements are secured to the tool base portion with an axle element, and
    a first tool element that is coupled together with a second tool element,
    wherein the first and second tool elements are configured to be positioned into an open tool exchange position so as to be able to be mounted on or removed from the tool base portion.

12. The device of claim 11, wherein the tool base portion comprises a first tool base segment and a second tool base segment, and wherein the first pulley element is rotatably coupled to the first tool base segment and the second pulley element is rotatably coupled to the second tool base segment.

13. The device of claim 11, wherein the first and second tool elements are removably and replaceably coupled to the tool base portion when disposed in the open tool exchange position.

14. The device of claim 11, wherein the first pulley element has a first pulley surface feature formed thereon and the second pulley element has a second pulley surface feature formed thereon, and wherein the first tool element has a first surface feature formed thereon that is complementary in shape to the first pulley surface feature of the first pulley element and the second tool element has a second surface feature formed thereon that is complementary in shape to the second pulley surface feature of the second pulley element, wherein when the first and second pulley surface features of the first and second pulley elements are aligned and when the first and second surface features of the first and second tool elements are aligned when disposed in the open tool exchange position, the first and second tool elements can be removably and replaceably mounted on the first and second pulley surface features of the first and second pulley elements, respectively.

15. The device of claim 14, wherein the first tool element has a first connection surface feature formed thereon and the second tool element has a second connection surface feature formed thereon that is complementary in shape to the first connection surface feature, such that the first and second connection surface features, when aligned, enable the first and second tool elements to be coupled together.

16. The device of claim 15, wherein the first connection surface feature includes a groove and the second connection surface feature includes a protruding rail-like element.

17. The device of claim 15, wherein the first and second connection surface features are configured to form a dovetail joint connection.

18. The device of claim 15, wherein when the first tool element and the second tool element are assembled, the first and second tool elements are locked together by selective rotation of one or more the first and second tool elements out of the open tool exchange position and into one or more use positions by rotational movement of one or more of the first and second pulley elements.

19. The device of claim 14, further comprising
a first conductive spring element that is coupled to the first pulley element and a second conductive spring element that is coupled to the second pulley element, and
a first conductive contact element that is coupled to the first tool element and a second conductive contact element that is coupled to the second tool element.

20. The device of claim 19, wherein a portion of the conductive spring element continually and directly contacts a portion of the conductive contact element, during use, and independent of a rotational position of the first and second pulley elements.

21. A wrist portion of a robot arm forming part of a robotic unit of a surgical robotic system, comprising
a tool base portion that is coupled to an end portion of the robot arm by a connector,
a first pulley element rotatably coupled to the tool base portion, wherein the first pulley element has a main body having a first pulley surface feature formed thereon,
a second pulley element rotatably coupled to the tool base portion, wherein the second pulley element has a main body having a second pulley surface feature formed thereon,
a first tool element having a main body having a first surface feature formed thereon that is complementary in shape to the first pulley surface feature of the first pulley element, and
a second tool element having a main body having a second surface feature formed thereon that is complementary in shape to the second pulley surface feature of the second pulley element,
wherein when the first pulley surface feature of the first pulley element and the second pulley surface feature of the second pulley element are aligned with each other when disposed in a first open tool exchange position, the first and second tool elements can be removably and replaceably mounted on the first and second pulley surface features of the first and second pulley elements, respectively.

22. The wrist portion of claim 21, wherein the tool base portion comprises a first tool base segment and a second tool base segment, and wherein the first pulley element is rotatably coupled to the first tool base segment and the second pulley element is rotatably coupled to the second tool base segment.

23. The wrist portion of the robot arm of claim 22, wherein when the first and second tool elements are removably mounted on the first and second pulley elements, the first surface feature of the first tool element mates with and seats on the first pulley surface feature of the first pulley element and the second surface feature of the second tool element mates with and seats on the second pulley surface feature of the second pulley element.

24. The wrist portion of the robot arm of claim 23, wherein each of the first and second pulley surface features is shaped and configured as a boss element and wherein each of the first and second surface features includes a slot.

25. The wrist portion of the robot arm of claim 23, wherein each of the first and second tool base segments has a main body having an extension portion at one end and a flange portion at an opposed end, wherein the extension portion has an inner surface and an opposed outer surface and has an aperture formed therein, and wherein the inner surface of the extension portion has a recess formed therein.

26. The wrist portion of the robot arm of claim 25, wherein the flange portion of each of the first and second tool base segments has an opening formed therein for seating the connector.

27. The wrist portion of the robot arm of claim 25, wherein each of the first and second pulley elements has a main body having an inner surface and an opposed outer surface having a connection element formed thereon and protruding outwardly therefrom, wherein the pulley surface features are formed on the inner surface of the main body.

28. The wrist portion of the robot arm of claim 27, wherein the main body of each of the first and second pulley elements has a plurality of holes formed therein, and wherein at least a portion of the plurality of holes are sized and configured for seating a portion of a control cable.

29. The wrist portion of the robot arm of claim 27, wherein the connection element of the first pulley element seats and is retained within the recess formed in the inner surface of the first tool base segment, and wherein the connection element of the second pulley element seats and is retained within the recess formed in the inner surface of the second tool base segment.

30. The wrist portion of the robot arm of claim 29, further comprising a first electrically conductive spring element coupled to the first pulley element and a second electrically conductive spring element coupled to the second pulley element.

31. The wrist portion of the robot arm of claim 30, wherein each of the first and second electrically conductive spring elements comprises a main body having a central coil element, a top tab portion coupled to one end of the coil element, and a bottom tab portion coupled to another end of the coil element.

32. The wrist portion of the robot arm of claim 31, wherein the bottom tab portion is coupled to an electrical lead wire housed within the tool base portion, and wherein the coil element is coupled to the outer surface of the pulley element and at least a portion of the top tab portion is coupled to the inner surface of the pulley element.

33. The wrist portion of the robot arm of claim 32, wherein, during use, the central coil element is configured to expand and contract based on movement of the top tab portion.

34. The wrist portion of the robot arm of claim 32, wherein each of the first and second tool elements has a working surface for contacting a workpiece, further comprising
- a first conductive contact element coupled to the working surface of the first tool element, and
- a second conductive contact element coupled to the working surface of the second tool element,
- wherein at least a portion of the first and second conductive contact elements are configured for contacting at least a portion of the top tab portion of the first and second conductive spring elements, respectively, when mounted to the first and second tool elements, respectively.

35. The wrist portion of the robot arm of claim 34, wherein the portion of each of the first and second conductive contact elements remains in continual electrical contact with the respective portion of the first and second conductive spring elements, during use.

36. The wrist portion of the robot arm of claim 34, wherein the first tool element has a main body having an outer surface and an opposed inner surface having a first tool surface feature associated therewith, and wherein the second tool element has a main body having an outer surface and an opposed inner surface having a second tool surface feature associated therewith, wherein the second tool surface feature is complementary in shape to the first tool surface feature.

37. The wrist portion of the robot arm of claim 36, wherein the first tool surface feature of the first tool element is a groove and the second tool surface feature of the second tool element is a protrusion.

38. The wrist portion of the robot arm of claim 37, wherein the groove and the protrusion are configured to form a dove-tail joint.

39. The wrist portion of the robot arm of claim 37, wherein each of the groove and the protrusion has a selected width, and wherein each of the groove and the protrusion has one or more narrow width sections and one or more widened width sections.

40. The wrist portion of the robot arm of claim 39, wherein the first and second tool elements are assembled together by arranging the first and second tool elements relative to each other such that the working surfaces of the first and second tool elements are separated by an angular distance greater than about 180 degrees such that the widened width sections of the protrusion are aligned with the widened width sections of the groove, and when the protrusion is inserted into the groove and the first and second tool elements are rotated relative to each other, the first and second tool elements are connected to each other.

41. The wrist portion of the robot arm of claim 21, further comprising
- a first electrically conductive spring element coupled to the first pulley element,
- 1a second electrically conductive spring element coupled to the second pulley element,
- a first conductive contact element coupled to the first tool element, and
- a second conductive contact element coupled to the second tool element.

42. The wrist portion of the robot arm of claim 41, wherein each of the first and second tool base segments, the first and second pulley elements, and the first and second tool elements has an opening formed therein for seating, when aligned together, an axle element for securing together the first and second tool base segments, the first and second pulley elements, and the first and second tool element.

* * * * *